United States Patent
Minion

(10) Patent No.: US 12,236,581 B2
(45) Date of Patent: Feb. 25, 2025

(54) SYSTEM AND METHOD FOR ANATOMIC CLASSIFICATION OF AORTIC ANATOMY IN ANEURYSMS

(71) Applicant: University of Kentucky Research Foundation, Lexington, KY (US)

(72) Inventor: David J Minion, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 435 days.

(21) Appl. No.: 16/953,027

(22) Filed: Nov. 19, 2020

(65) Prior Publication Data

US 2021/0150708 A1 May 20, 2021

Related U.S. Application Data

(60) Provisional application No. 62/937,686, filed on Nov. 19, 2019.

(51) Int. Cl.
*G06T 7/00* (2017.01)
*A61F 2/07* (2013.01)
*G06T 7/13* (2017.01)

(52) U.S. Cl.
CPC .............. *G06T 7/0012* (2013.01); *A61F 2/07* (2013.01); *G06T 7/13* (2017.01); *G06T 2207/20041* (2013.01); *G06T 2207/20081* (2013.01); *G06T 2207/30101* (2013.01)

(58) Field of Classification Search
CPC ...... G06T 7/0012; G06T 7/13; G06T 2207/20041; G06T 2207/20081; G06T 2207/30101; A61F 2/07
See application file for complete search history.

(56) References Cited

U.S. PATENT DOCUMENTS

| 7,027,630 | B2* | 4/2006 | Bruijns ............... G06T 17/00 382/154 |
| 7,048,716 | B1* | 5/2006 | Kucharczyk ........ G01R 33/285 604/164.01 |
| 9,367,667 | B2* | 6/2016 | Baloch ................ G06N 20/00 |
| 9,968,409 | B2* | 5/2018 | Yagi ........................ A61F 2/95 |
| 10,111,636 | B2* | 10/2018 | Itu ............................ G06T 7/11 |

(Continued)

OTHER PUBLICATIONS

Kohout, Josef, et al. "Aneurysm identification by analysis of the blood-vessel skeleton." Computer methods and programs in biomedicine 109.1 (2013): 32-47.*

(Continued)

*Primary Examiner* — Shefali D Goradia
(74) *Attorney, Agent, or Firm* — Stites & Harbison PLLC; James R. Hayne

(57) ABSTRACT

A method of anatomic classification of blood vessel anatomy in aneurysms includes the steps of accessing an image of a blood vessel, analyzing the image to identify a point of divergence of the blood vessel and one or more additional points of reference of the blood vessel. One or more distances are then measured between the point of divergence of the blood vessel and at least one of the one or more additional points of reference. The aneurysm is then classified based upon the measured distances. A method of treatment of an aneurysm in a blood vessel further includes implanting one or more devices within the blood vessel for treatment of the aneurysm.

14 Claims, 25 Drawing Sheets

(56) References Cited

U.S. PATENT DOCUMENTS

2012/0310085 A1* 12/2012 Herweck .............. A61B 8/0841
                                                      604/529
2015/0073523 A1*  3/2015 Chobotov ................ A61F 2/07
                                                      623/1.13

OTHER PUBLICATIONS

Lauric, Alexandra, et al. "Automated detection of intracranial aneurysms based on parent vessel 3D analysis." Medical image analysis 14.2 (2010): 149-159.*

Cebral, Juan R., et al. "Efficient pipeline for image-based patient-specific analysis of cerebral aneurysm hemodynamics: technique and sensitivity." IEEE transactions on medical imaging 24.4 (2005): 457-467.*

Kerrien, Erwan, et al. "Blood vessel modeling for interactive simulation of interventional neuroradiology procedures." Medical image analysis 35 (2017): 685-698.*

Kang, Dong-Goo, Dae Chul Suh, and Jong Beom Ra. "Three-dimensional blood vessel quantification via centerline deformation." IEEE Transactions on Medical Imaging 28.3 (2008): 405-414.*

Bell, Vanessa, et al. "Longitudinal and circumferential strain of the proximal aorta." Journal of the American Heart Association 3.6 (2014): e001536.*

* cited by examiner

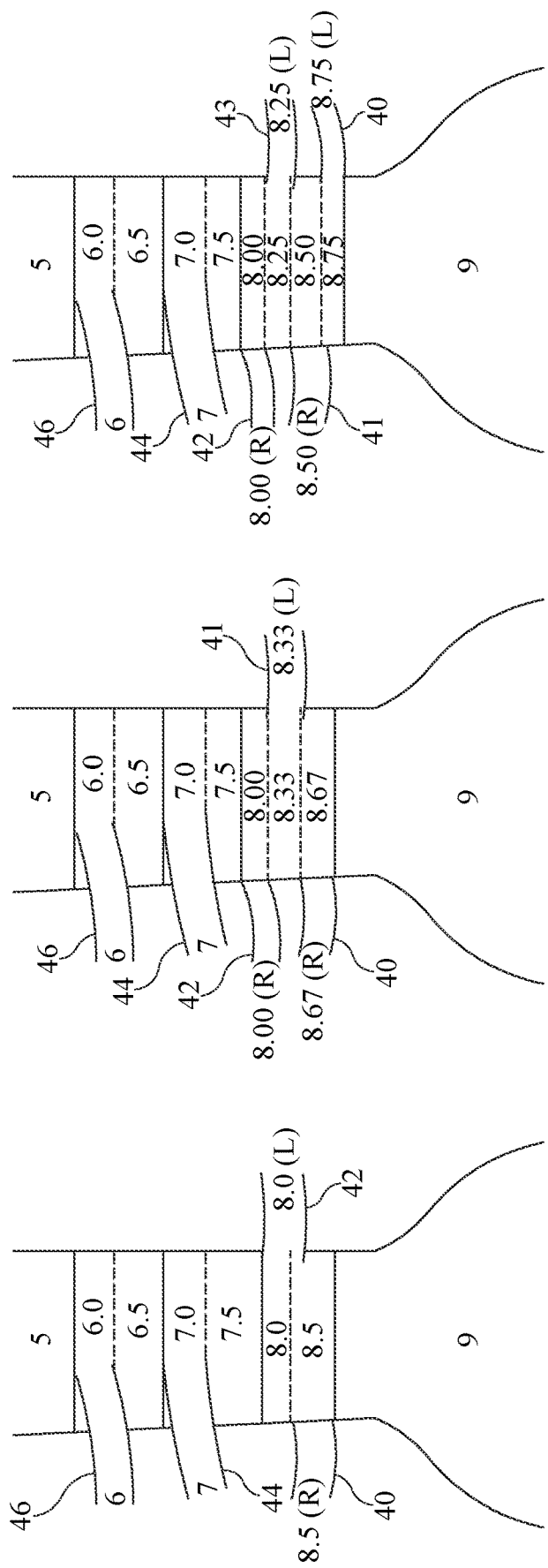

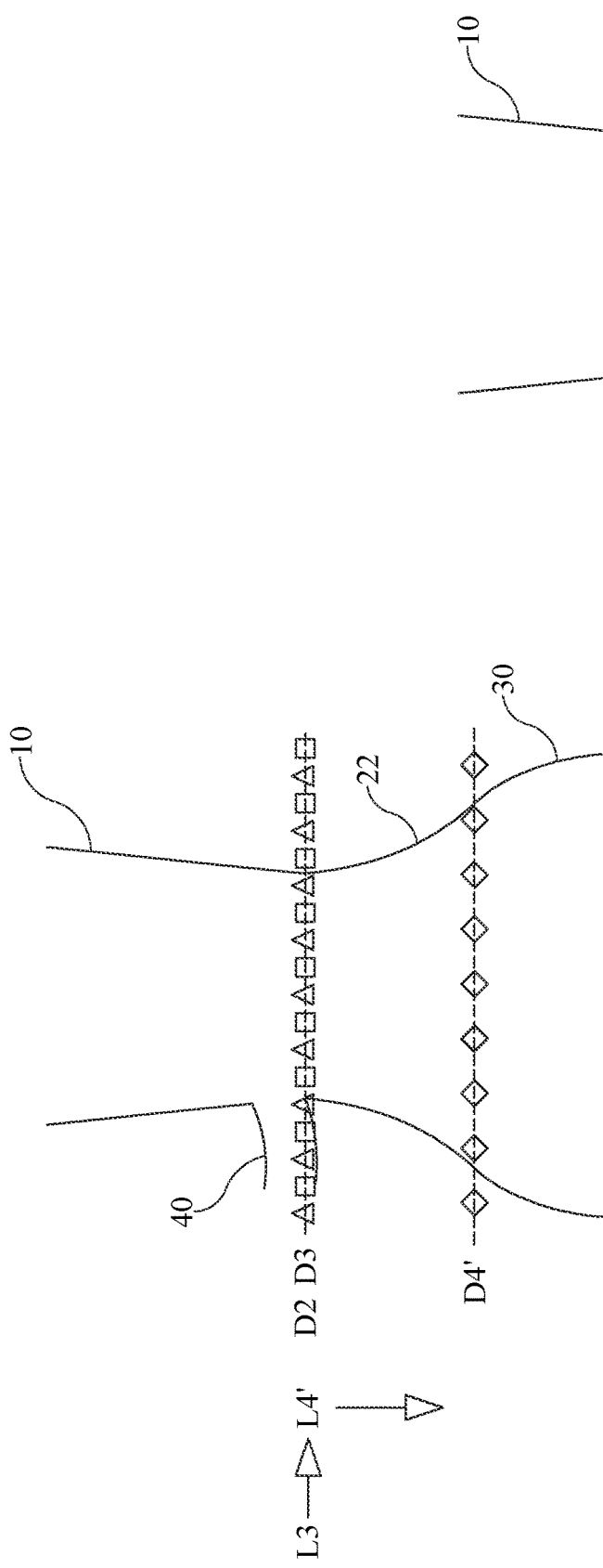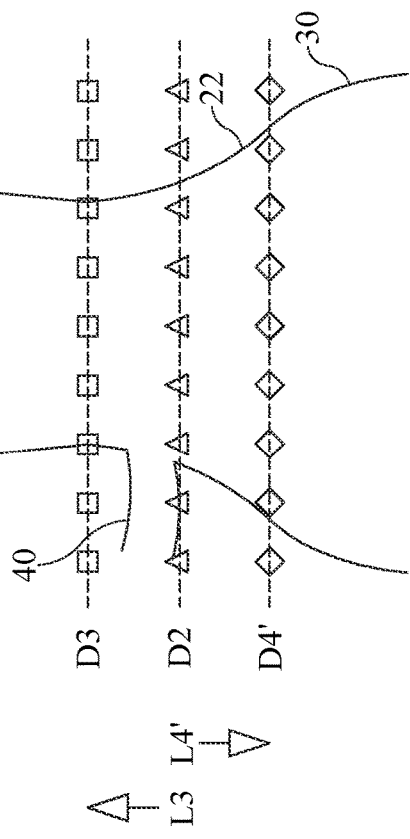
FIG. 9A
FIG. 9B

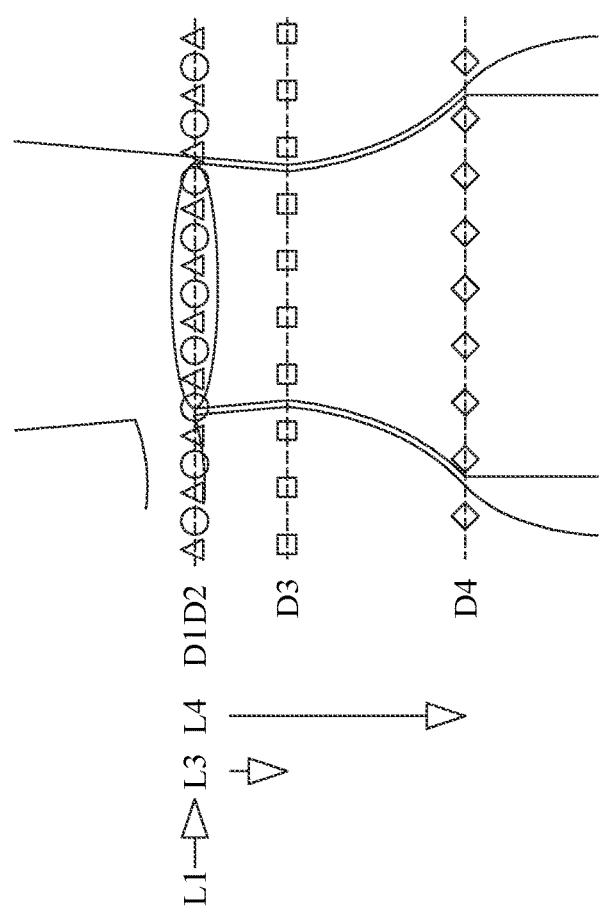
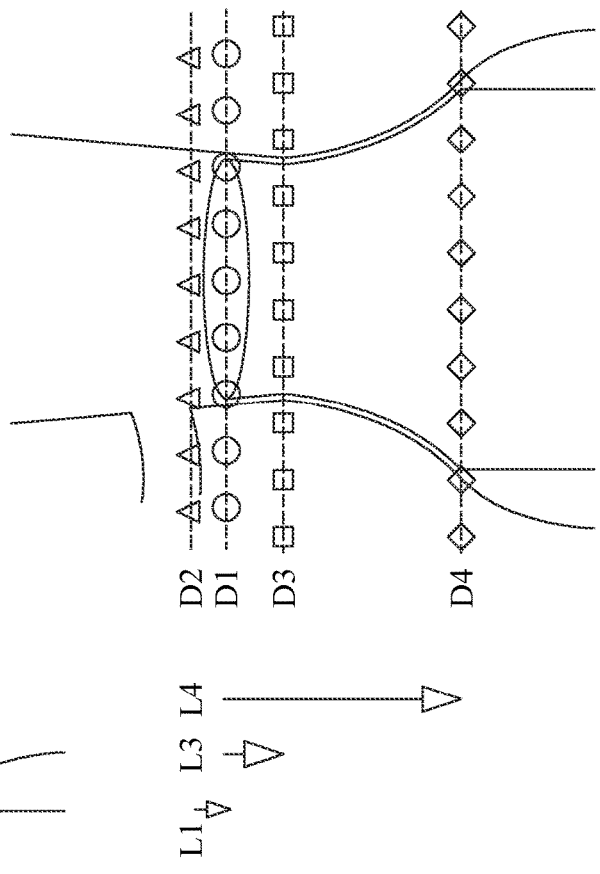
FIG. 12A
FIG. 12B

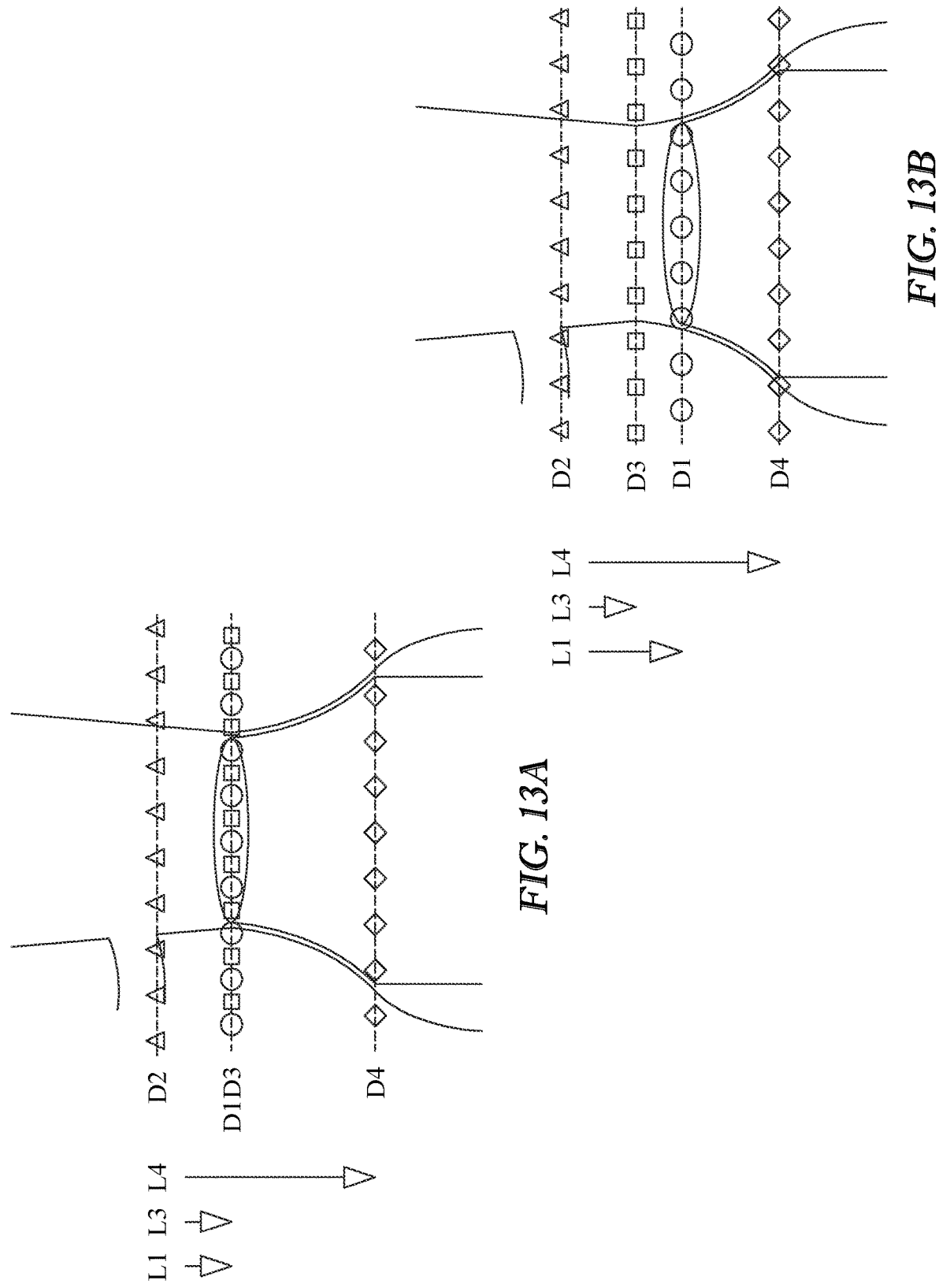

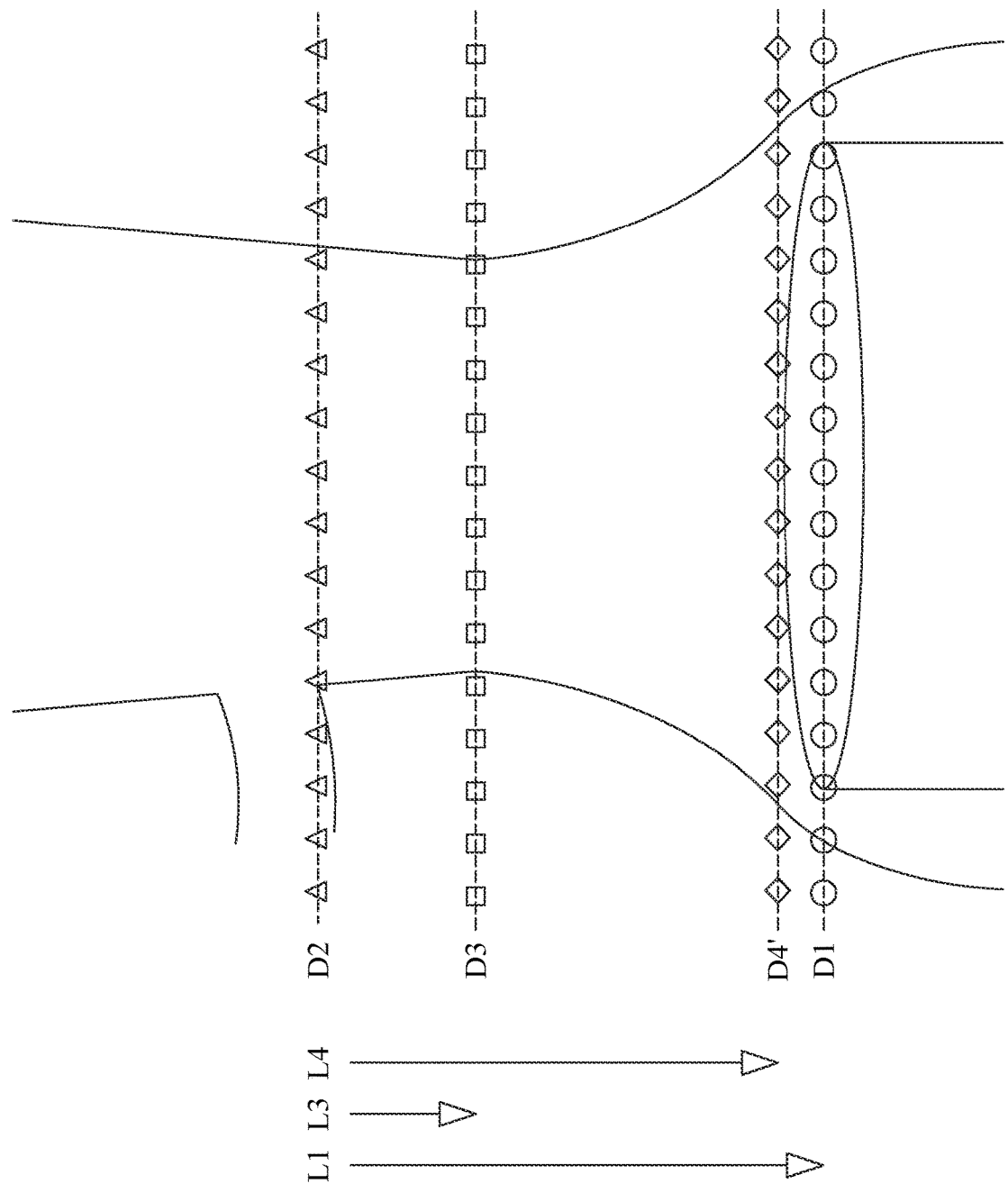

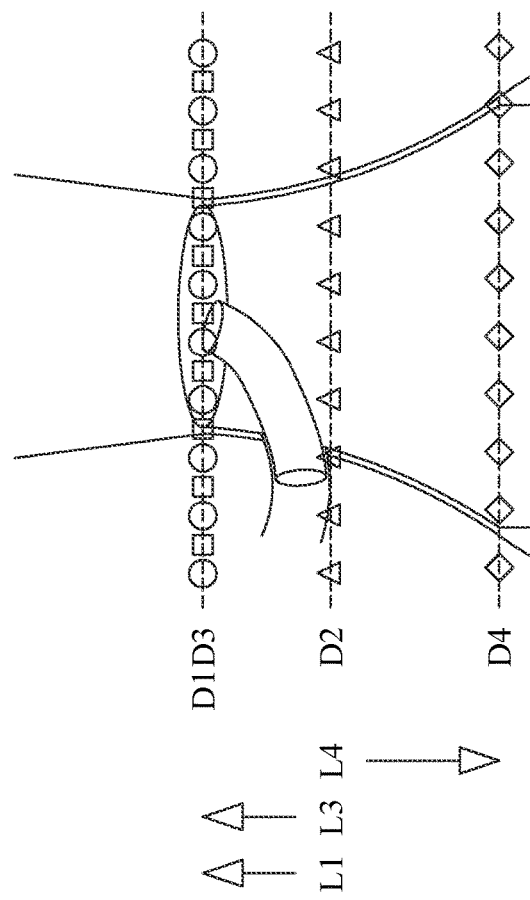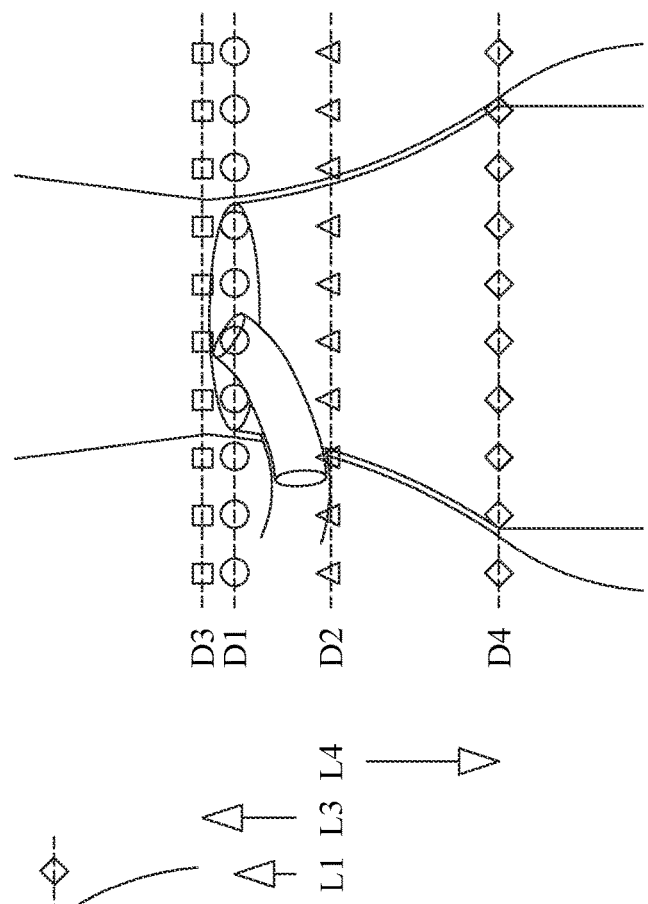
FIG. 16A
FIG. 16B

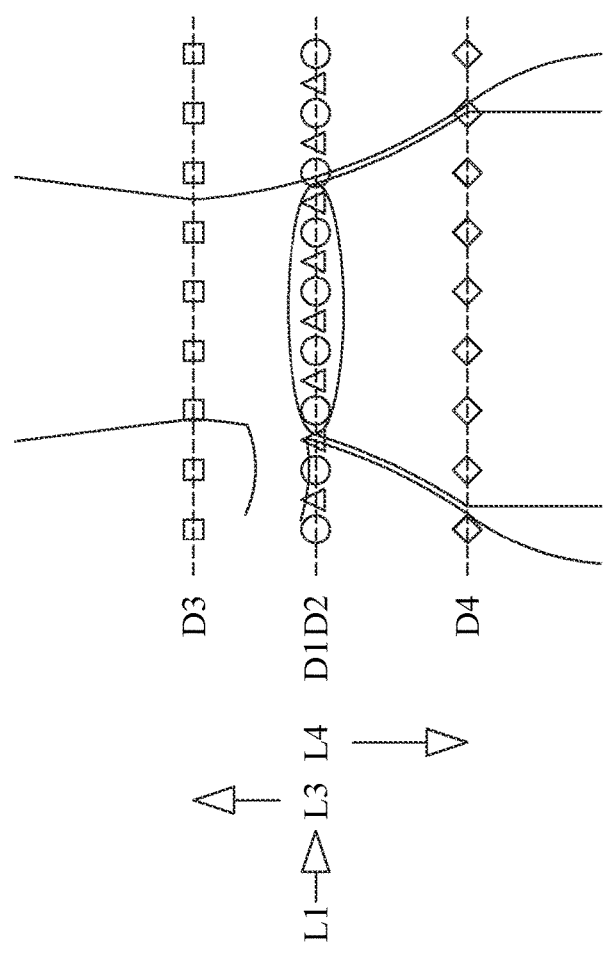
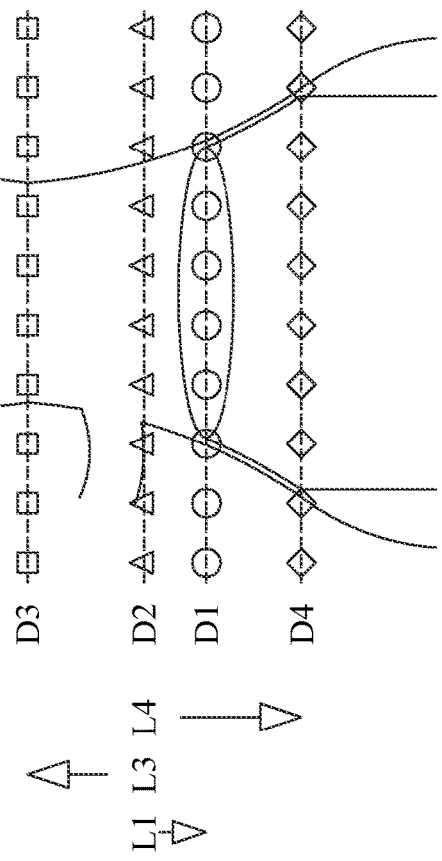
FIG. 17A
FIG. 17B

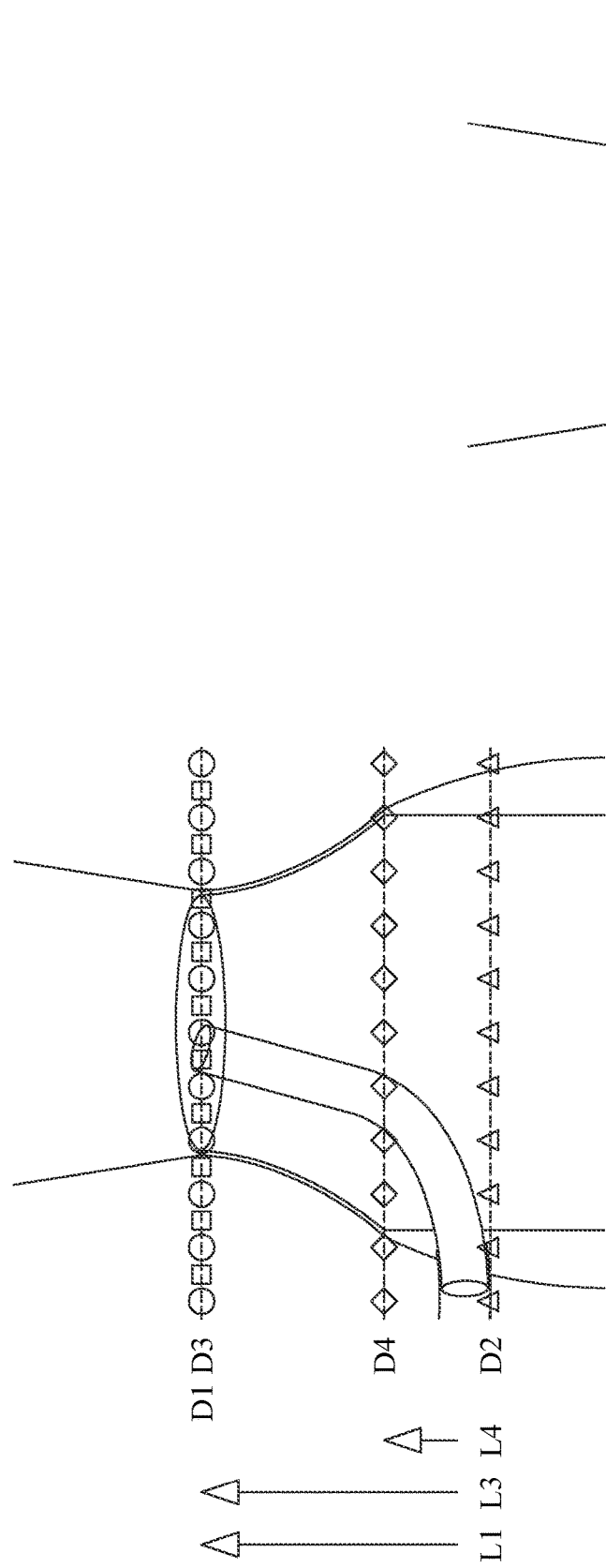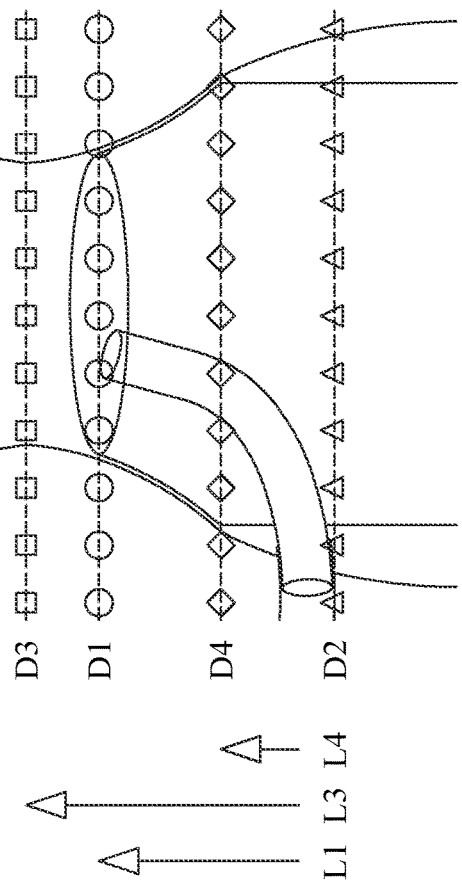
FIG. 20A
FIG. 20B

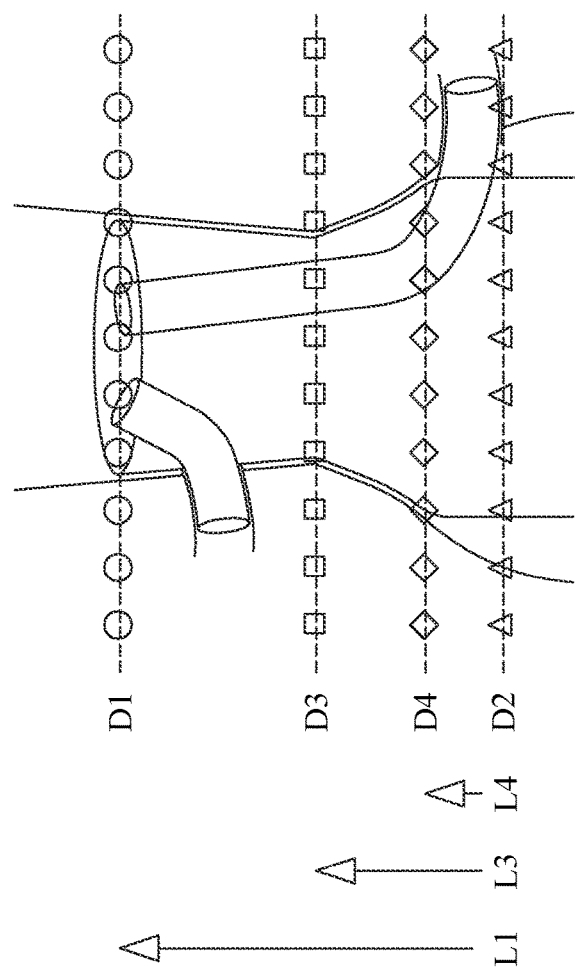
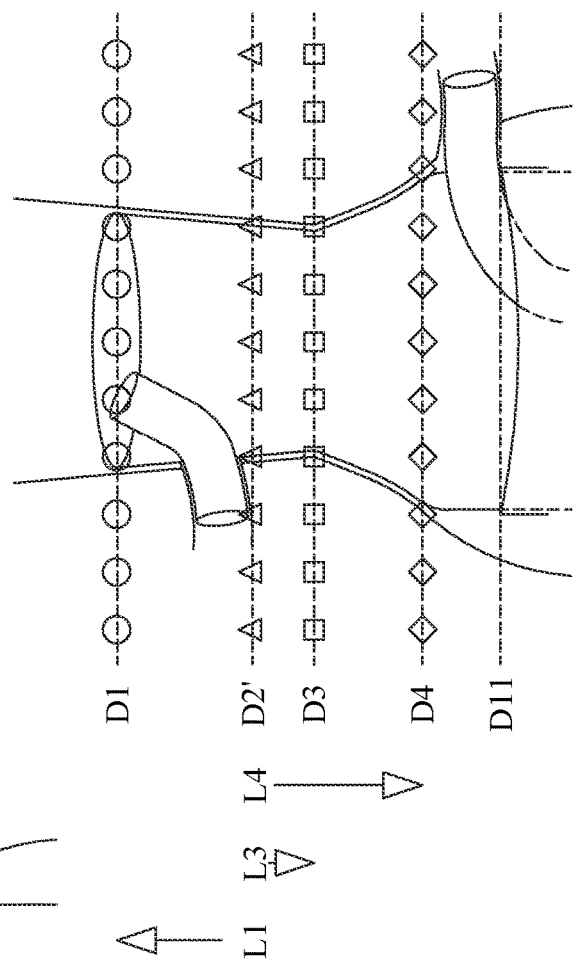
FIG. 24A
FIG. 24B

SYSTEM AND METHOD FOR ANATOMIC CLASSIFICATION OF AORTIC ANATOMY IN ANEURYSMS

CROSS-REFERENCE TO RELATED APPLICATIONS

The present application claims priority to U.S. Provisional Patent Application Ser. No. 62/937,686 filed on Nov. 19, 2019, the entire disclosures of which are incorporated herein by reference.

TECHNICAL FIELD

The present disclosure relates generally to aneurysms and their treatment. More particularly, the disclosure relates to a system and method of defining and classifying aneurysm morphology that can be used for evaluation of various treatment options and establish guidelines and indications for repair.

BACKGROUND OF THE INVENTION

Outcomes research in medicine is a broad field of research that seeks to understand the comparative effectiveness of different treatment options for any number or variety of outcome parameters. As such, it is a key component of quality initiatives that seek to develop and refine evidence-based guidance for improved care and cost-effectiveness in the practice of medicine. Critical to its success is the ability to identify and control for the numerous variables that may impact the outcome parameter of interest.

Endovascular aneurysm repair (EVAR) has become a popular, if not the preferred, treatment strategy for aortic aneurysms. The core outcome that this strategy aims to impact is aneurysm rupture.

By definition, an aneurysm is a localized dilation in a blood vessel caused by or resulting in a weakening of the vessel wall. The pathophysiologic mechanisms for aneurysm development are quite complex, but central to the process is intraluminal pressure (i.e., blood pressure.) Unfortunately, since the same intraluminal pressure results in greater wall tension as the diameter of the vessel increases, aneurysmal disease is a self-sustained progressive degeneration. Ultimately, the degeneration can lead to rupture of the weakened wall and acute hemorrhagic blood loss, which is often a fatal event.

The earliest treatment of aneurysms involved ligation, effectively cutting off all pressure to the aneurysm, but also cutting off all flow through the blood vessel. Therefore, this strategy alone is rarely practical due to the potential ischemic complications from loss of blood supply to the structures sub-served by the ligated blood vessel. Another early treatment strategy involved wrapping of the aneurysm in an attempt to re-enforce the vessel wall. Although this strategy maintained flow through the blood vessel, it had significant morbidity and only haphazard success.

The development of synthetic vascular grafts in the 1950's ushered in an era of replacement of the diseased portion of the blood vessel through open surgical techniques. While this strategy surgically removes the aneurysm from the pressurized vascular system while maintaining blood flow through the newly inserted synthetic conduit, the pathophysiologic stress and potential for complications of these procedures is significant, especially when involving the aorta.

Endovascular aneurysm repair (EVAR) is a strategy that also attempts to exclude the aneurysm from pressure while maintaining blood flow but uses a minimally invasive approach. In its simplest conception, endovascular repair could be considered analogous to inserting an inner tube, or liner, in the diseased blood vessel. For success, the inner synthetic tube must be impervious to blood in order to contain the blood pressure from being transmitted to the aneurysm wall. As such, the devices used for this strategy usually combine an impervious fabric (or graft) with an expandable metal scaffolding (or stent) and are therefore often referred to as "stent-grafts." A broader terminology that is independent of construction design includes "endograft" or "endoprosthesis."

In addition to having an impervious outer boundary, the endograft also cannot be free floating in the aneurysm since that would still allow blood pressure to be transmitted around the graft to the aneurysm wall. Rather, the endograft must be affixed to normal or near normal vessel both proximal and distal to the aneurysmal portion through which it traverses. These segments of non-aneurysmal vessel used for attachment proximal and distal to the aneurysm are commonly known as seal zones and are critical to the success of the procedure.

For standard cases of EVAR, the sealing segments in aorta are both normal in caliber and devoid of any branch points. The endograft is sized to fit snugly inside of the aortic sealing segment to provide circumferential apposition, preventing any blood pressure from being transmitted around the endograft to the aneurysm. If secure and complete circumferential apposition is not achieved and blood pressure is transmitted with any flow around the graft then the aneurysm has not been excluded and remains at risk for rupture. Continued flow or pressure into the aneurysm sac after EVAR is known as an endoleak. When the endoleak is related to flow around the endograft due to impaired apposition in the seal zone, it more specifically known as a Type I Endoleak.

In some cases, the sealing segment in the aorta contains branches supplying critical organs or vital structures such as the kidneys or intestines. In these cases, if a standard endograft were placed in these aortic segments it would cover the orifices to these branch vessels and cut-off blood supply to the vital structures supplied by the branches. A similar phenomenon would occur if a critical branch vessel arose from the aneurysm itself. As such, more complex device options have been developed to maintain branch vessel perfusion in these cases of more complex anatomy.

One design option involves incorporating orifices (known as fenestrations) in the endograft that can be aligned with orifices of branch vessels. Another option (appropriately known as branched grafts) involves incorporating branches onto the endograft that can be extended into the critical branch vessels. A third commonly used option (known as parallel grafts) is to place a device, usually a smaller stent graft, alongside the main graft and extending into the branch vessel to maintain an accessory channel in the seal zone that supplies the branch vessel. The accessory devices are also often referred to as "snorkel" or "chimney" grafts.

Although the interaction between the sealing segments of the treated vessels and the endoprosthesis is arguably the most important factor in the success of endovascular aneurysm repair, outcomes research has suffered from a lack of consensus definitions and simplified protocols that provide specific anatomic detail for sophisticated analysis. In particular, for abdominal aortic aneurysms, the anatomy of the proximal seal zone is considered the most critical in terms of chance for success and the appropriateness for endovascular. The portion of that seal zone distal to the renal arteries is referred to specifically as the neck. If the neck is of adequate health and length, then complex strategies such as fenestrated, branched, or parallel graft repair are unnecessary since the orifices of the important branch vessels do not need to be covered. Unfortunately, even the seemingly straightforward task of determining the length of neck in this critical infrarenal segment remains elusive.

The challenge in defining and adequately characterizing the neck is that there is rarely an abrupt transition from normal aorta to dilated aneurysmal aorta. More often, there is an indistinct transition to the grossly diseased aneurysmal segment. In some cases, the transition is quite gradual. This shape, similar to that of a tall thin Christmas tree, is referred to as "reverse conical" or "reverse taper." In addition, there are other disease processes such as calcification or mural thrombus that could have a detrimental effect on the sealing interaction if present in the neck. Such "hostile" characteristics have consistently been shown to be associated with an approximately fourfold risk of late failure compared to "favorable" anatomy and recent evidence suggest that reverse conical morphology is the single most significant of these hostile features.

Unfortunately, the degree of reverse conicity that is acceptable for EVAR, or even how to measure it, also remains elusive. Obviously, when evaluating any segment such as that of the immediate infrarenal aorta, the measured length of the neck will be partly determined by the degree of reverse conicity that is determined acceptable. For example, accepting 20% reverse conicity will result in a longer neck length determination than if only 10% reverse conicity were considered acceptable.

Further complicating the issue is that any potential seal zone may be comprised of multiple subsegments of seal zones of varying degrees of favorable versus hostile characteristics. In such cases, the seal zones could be characterized by their most favorable segments, their least favorable segments, all segments separately, all segments on average, or many other combinations. Adding in other variables such as the construct of the endograft and the adequacy of the suprarenal segment used in a complex repair, it becomes clear that any system designed to characterize the anatomy used in EVAR must be able to define, identify, and classify a wide range of scenarios. The key for outcomes research is that such characterization is done in a simplified, efficient, and reproducible manner.

SUMMARY OF THE INVENTION

In accordance with the foregoing need identified in the art as described herein, a system of defining and classifying aortic aneurysm anatomy is provided. The disclosed system utilizes objective and easily identifiable points of reference. In the system, the diameter and relative location of the points of reference are then used in a formulaic manner to define and characterize sealing segments and other anatomic variables. Further, the pattern or anatomic order of multiple points of reference establish phenotypes for grouping and comparing individual morphologies.

One exemplary method of anatomic classification of blood vessel anatomy in aneurysms comprises accessing an image of a blood vessel; analyzing the image to identify a point of divergence of the blood vessel and one or more additional points of reference of the blood vessel; measuring one or more distances between the point of divergence of the blood vessel and at least one of the one or more additional points of reference; and classifying the aneurysm based upon the measured distances.

In some exemplary implementations, the one or more additional points of reference includes at least one of: (i) an origin of the blood vessel, (ii) a terminus of the blood vessel, (iii) a location of one or more branch vessels, (iv) a location of a lowest preserved branch vessel, (iv) a point of threshold diameter of the blood vessel, (v) a point of restriction of the blood vessel, (vi) a point of maximum diameter of the blood vessel, and (vii) a point of convergence of the blood vessel In some exemplary implementations, when a device is already implanted within the blood vessel, the image is further analyzed to identify at least one of: a proximal end of the device, and an end of apposition of the device. In such instances, according to some embodiments, the threshold diameter of the blood vessel is a maximum diameter of therapeutic effectiveness of the device. Likewise, in some embodiments, the threshold diameter of the blood vessel is a maximum diameter of the device.

In some exemplary implementations, one of the one or more distances measured is a distance between the point of divergence of the blood vessel and the location of the lowest preserved branch vessel. In some exemplary implementations, one of the one or more distances measured is a distance between the point of divergence of the blood vessel and the point of threshold diameter of the blood vessel. In some exemplary implementations, one of the one or more distances measured is a distance between the proximal end of the device and the location of the lowest preserved branch vessel. In some exemplary implementations, one of the one or more distances measured is a distance between the point of divergence of the blood vessel and a point where a diameter of the blood vessel is a maximum diameter of therapeutic effectiveness of the device.

In some exemplary implementations, the classification of the aneurysm includes identifying the following segments of the blood vessel: a seal zone proximal to the point of divergence; a sub-seal zone distal to the point of divergence, but proximal to the point of threshold diameter of the blood vessel; and an aneurysm sac distal to the point of threshold diameter of the blood vessel.

In some exemplary implementations, the classification of the aneurysm further includes determining which of the segments of the blood vessel contains a lowest preserved branch vessel.

One exemplary method of treatment of an aneurysm in a blood vessel comprises analyzing an image of a blood vessel to identify a point of divergence of the blood vessel and a point of threshold diameter of the blood vessel; identifying the following features of the blood vessel: (i) a seal zone proximal to the point of divergence of the blood vessel, (ii) a sub-seal zone distal to the point of divergence of the blood vessel, but proximal to the point of threshold diameter of the blood vessel, and (iii) an aneurysm sac distal to the point of threshold diameter of the blood vessel; and implanting one or more devices, such as a parallel endograft within the blood vessel for treatment of the aneurysm.

In some exemplary implementations, an external portion of a parallel branch stent of the parallel endograft does not cross the point of the threshold diameter of the blood vessel to reach a branch vessel in the aneurysm sac.

In some exemplary implementations, an external portion of a parallel branch stent of the parallel endograft does not cross the point of the threshold diameter of the blood vessel or the point of divergence of the blood vessel to reach a branch vessel in the sub-seal zone.

In some exemplary implementations, an external portion of a parallel branch stent of the parallel endograft does not cross the point of divergence of the blood vessel to reach a branch vessel in the seal zone.

An exemplary system for anatomic classification of blood vessel anatomy in aneurysms, comprises a data receiving module for receiving an image of a blood vessel; and an analysis module for (i) analyzing the image to identify a point of divergence of the blood vessel and one or more additional points of reference of the blood vessel, (ii) measuring one or more distances between the point of divergence of the blood vessel and at least one of the one or more additional points of reference, and (iii) classifying the aneurysm based upon the measured distances.

DESCRIPTION OF THE DRAWINGS

FIG. 4A depicts the proximal end of an aortic aneurysm illustrating the numbered zone system of the present invention;

FIG. 4B depicts the proximal end of another aortic aneurysm with an accessory renal artery illustrating the numbered zone system of the present invention;

FIG. 4C depicts the proximal end of another aortic aneurysm with multiple accessory renal arteries illustrating the numbered zone system of the present invention;

FIG. 9A depicts the proximal end of an aortic aneurysm demonstrating a Phenotype B;

FIG. 9B depicts the proximal end of an aortic aneurysm demonstrating a Phenotype B;

FIG. 12A depicts the proximal end of an aortic aneurysm of a patient's vasculature with a graft deployed within the vasculature demonstrating a Sub-Phenotype A2;

FIG. 12B depicts the proximal end of an aortic aneurysm of a patient's vasculature with a graft deployed within the vasculature demonstrating a Sub-Phenotype A2;

FIG. 13A depicts the proximal end of an aortic aneurysm of a patient's vasculature with a graft deployed within the vasculature demonstrating a Sub-Phenotype A1;

FIG. 13B depicts the proximal end of an aortic aneurysm of a patient's vasculature with a graft deployed within the vasculature demonstrating a Sub-Phenotype A1;

FIG. 14 depicts the proximal end of an aortic aneurysm of a patient's vasculature with a graft deployed within the vasculature demonstrating a Sub-Phenotype A0;

FIG. 16A depicts the proximal end of an aortic aneurysm of a patient's vasculature with a graft deployed within the vasculature demonstrating a Sub-Phenotype B2;

FIG. 16B depicts the proximal end of an aortic aneurysm of a patient's vasculature with a graft deployed within the vasculature demonstrating a Sub-Phenotype B2;

FIG. 17A depicts the proximal end of an aortic aneurysm of a patient's vasculature with a graft deployed within the vasculature demonstrating a Sub-Phenotype B1;

FIG. 17B depicts the proximal end of an aortic aneurysm of a patient's vasculature with a graft deployed within the vasculature demonstrating a Sub-Phenotype B1;

FIG. 20A depicts the proximal end of an aortic aneurysm of a patient's vasculature with a graft deployed within the vasculature demonstrating a Sub-Phenotype C1;

FIG. 20B depicts the proximal end of an aortic aneurysm of a patient's vasculature with a graft deployed within the vasculature demonstrating a Sub-Phenotype C1;

FIG. 24A depicts the proximal end of an aortic aneurysm of a patient's vasculature with a parallel graft deployed within the vasculature that cross the Point of Divergence and the End of Apposition;

FIG. 24B depicts the proximal end of an aortic aneurysm of a patient's vasculature with a parallel graft deployed within the vasculature in which the lowest branch vessel is preserved in retrograde fashion;

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Embodiments of the system as disclosed herein provide for defining and classifying aortic aneurysm anatomy according to diameters at multiple points of reference.

Figure 1:
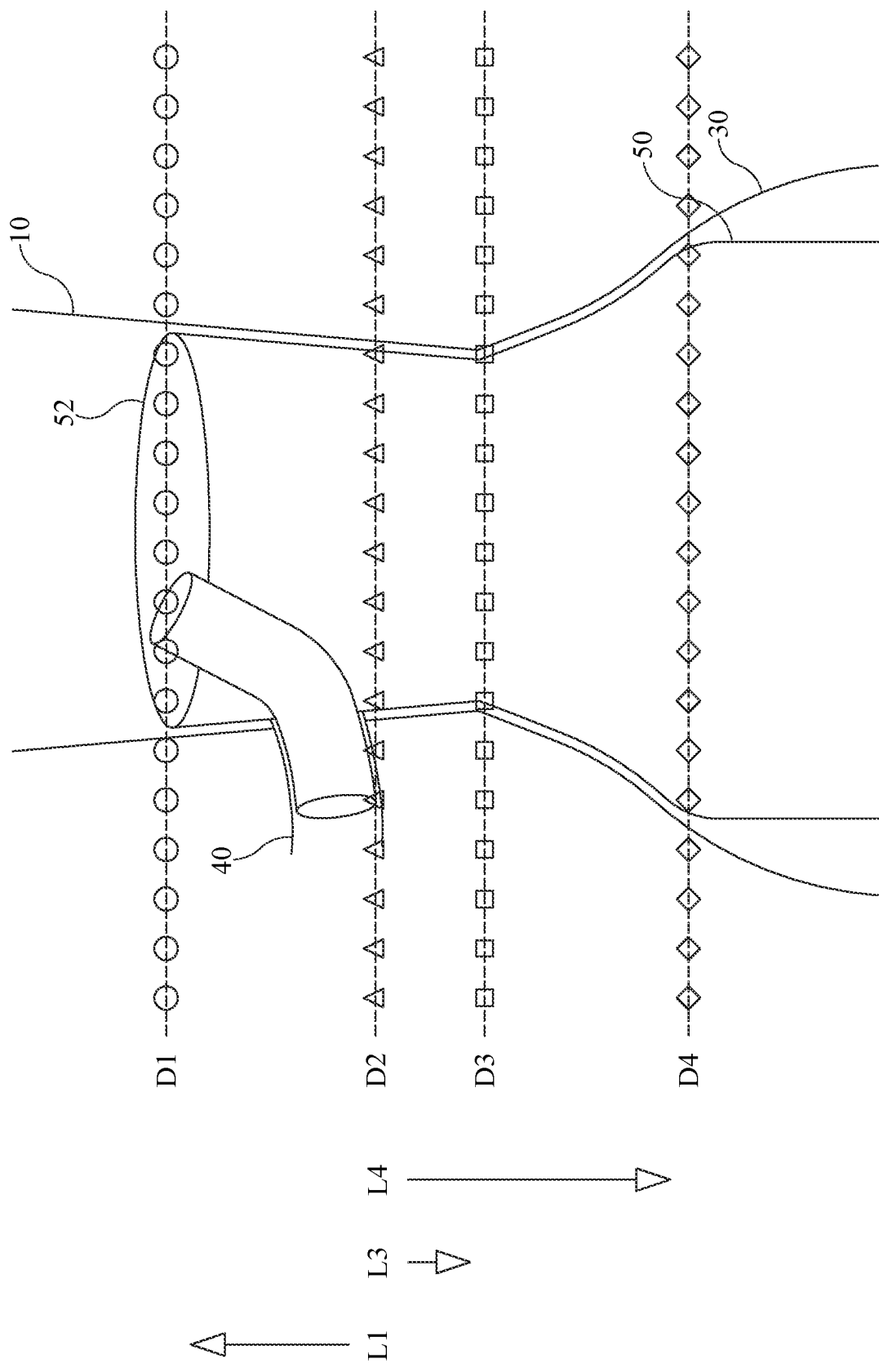
FIG. 1 depicts the proximal end of an aortic aneurysm of a patient's vasculature with a graft deployed within the vasculature.

With reference to the embodiment of FIG. 1, an aorta 10 of a patient, in which an aneurysm 30 has formed, includes a proximal treatment segment defined by the diameters at four points of reference (D1-D4) and their relative position (L1-L4) to characterize the interaction between a device, such as the endograft 50 illustrated in FIG. 1, and the proximal seal zone of the aorta 10. As used herein, the diameters are taken to be the outer diameter of the blood vessel. However, inner diameter measurements can also be utilized without departing from the spirit and scope of the present invention.

A first diameter, D1, indicates the Start of Devices. In the embodiment illustrated in FIG. 1, the Start of Devices is defined as the most proximal end 52 of the fabric covered portion of the main aortic endograft 50 that is at least partially apposed to the wall of the aorta 10. However, generally speaking, D1 indicates the most proximal extent of any therapies used in the treatment of an aneurysm.

A second diameter, D2, indicates a Lowest Preserved Branch Vessel (LPBV) of the aorta. The Lowest Preserved Branch Vessel refers to the pertinent branch vessels of the proximal sealing segment and is defined as the aortic diameter at the distal edge of the orifice of the most distal preserved branch vessel 40 of that segment. In most cases, including pre-operative morphology assessment, and as illustrated in FIG. 1, the Lowest Preserved Branch Vessel will be the more distal renal artery 40.

A third diameter, D3, indicates a Point of Divergence (POD) of the aorta 10. The Point of Divergence is defined as the point where the aortic contour changes from a cylindrical or conical shape to a reverse conical shape. In other words, it is the point where the diameter of the aorta 10 begins to increase (i.e., the walls diverge) in relation to the immediately proximal segment.

A fourth diameter, D4, indicates End of Apposition (EOA). The End of Apposition is defined as the most distal point in the proximal sealing segment where the endograft 50 still maintains contact with the wall of the aorta 10. As such, it is dependent on the diameter of the endograft 50 used in the repair. For pre-operative assessment, a pre-operative fourth diameter, D4' (shown in FIG. 3), is defined as the point distal to the Point of Divergence where the aortic reaches a threshold diameter. In some embodiments, the threshold diameter is between about 10 mm and about 50 mm, between about 20 mm and about 40 mm, or between about 30 mm and about 35 mm. In one particular exemplary embodiment, the threshold diameter is about 32 mm, as this diameter approximates the maximum sealing diameter of the currently available infrarenal devices. Generally speaking, the fourth diameters D4, D4' indicate the point where the diameter of the aorta 10 exceeds a maximum diameter of therapeutic effectiveness of a device used in the treatment of the blood vessel, either theoretical (D4') or realized (D4).

According to exemplary implementations of the present invention, after receiving or otherwise accessing an image of a blood vessel (e.g., an aorta), the image if analyzed to identify the location of these four points of reference of the blood vessel (D1-D4). The relative locations of these four points (D1-D4) are reduced to three length, or distance, measurements (L1, L3, L4), all based on the location of D2 (Lowest Preserved Branch Vessel). The lengths, L1, L3, L4 are defined as the longitudinal distance from each respective point of reference to D2. They are expressed as a positive value when the respective point of reference is distal to D2. They are expressed as a negative value when the respective point of reference is proximal to D2. With continued reference to FIG. 1, L1 is the longitudinal distance of D1 (Start of Devices) to D2 (Lowest Preserved Branch Vessel); L3 is the longitudinal distance of D3 (Point of Divergence) to D2 (Lowest Preserved Branch Vessel); and L4 is the longitudinal distance of D4 (End of Apposition) to D2 (Lowest Preserved Branch Vessel.) From these seven data points, numerous anatomic characteristics can be calculated or inferred.

As used herein, the Point of Divergence (D3) is considered the boundary marking the distal extent of the normal seal zone and the proximal extent of the aneurysm. This definition was chosen for a number of reasons. First, rather than relying on a subjective evaluation of the sealing adequacy of a vessel segment, it is an objectively defined point. Second, normal vessels are cylindrical or slightly conical in morphology. That is, the diameter of normal vessels gradually decreases from proximal to distal. While a vessel segment is conventionally considered aneurysmal once its diameter reaches 1.5 to 2 times that of a normal vessel, any dilation is abnormal by strict definition. Therefore, it is contended that reverse conical morphology is more appropriately included as part of the aneurysmal disease process rather than as part of the normal proximal segment.

However, it must also be recognized that reverse conical segments within the sealing diameter of the some endografts known in the art can still contribute to the sealing mechanism, even if they are diseased by strictest definition. As used herein, such an interaction is referred to as "Sub-Seal" to differentiate from the more robust sealing interaction in normal cylindrical or conical segments. The Sub-Seal zone extends from the Point of Divergence (D3) to the End of Apposition (D4). Mathematically, the length of this segment can be derived as L4 minus L3. It should be noted that the actual length of Sub-Seal achieved is not only dependent on the diameter of endograft but also its positioning in the potential Sub-Seal segment. Therefore, the Sub-Seal length (actual) can be determined mathematically as the lesser of (L4–L3) versus (L4–L1).

Since the term "Seal" as used herein is reserved only for cylindrical or conical segments of the blood vessel, the length of Seal extends from the Start of Devices (D1) to the Point of Divergence (D3) and is expressed mathematically as L3 minus L1. The Total Apposition Length (TAL) extends from the Start of the Devices (D1) to the End of Apposition (D4) and is defined as the sum of the Seal and Sub-Seal lengths. It can also be determined mathematically as L4 minus L1.

The Seal and the Sub-Seal can be further differentiated by the involvement of branch vessels in their respective aortic segments. Since the presence of such branch vessels requires more complex strategies (such as fenestrated, branched, or parallel grafts) for their preservation during endovascular repair, Seal and Sub-Seal segments proximal to the Lowest Preserved Branch Vessel (D2) are distinguished as "Complex" Seal and Sub-Seal segments. Those segments distal to the lowest preserved branch vessel (D2) can be treated with standard endografts and are therefore distinguished as "Standard" Seal and Sub-Seal segments.

As noted previously, the term "Neck" has historically denoted the infrarenal segment of potential seal in the aorta. As used herein, the term "Neck" is reserved for the portion of the cylindrical or conical potential infra-branch sealing segment and is analogous to Standard Seal. Mathematically, the Neck corresponds to the greater of L3 versus zero (since L3 will otherwise have a negative value if the Point of Divergence is proximal to the lowest renal artery.)

Figure 2C:
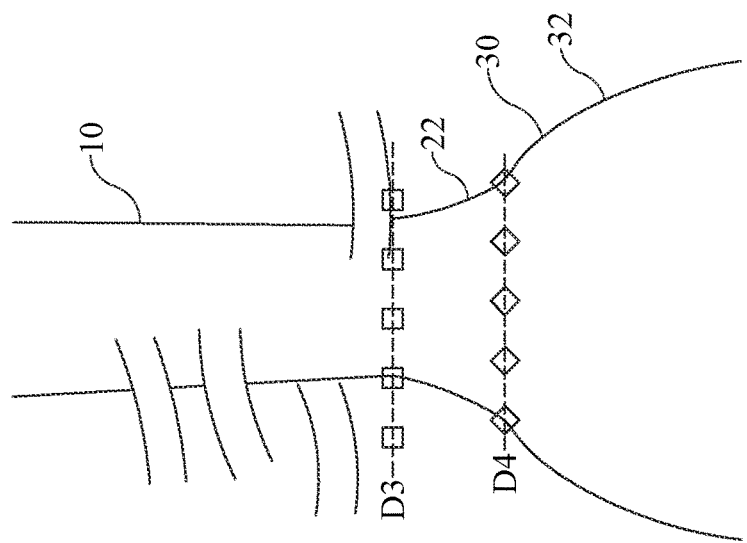
FIG. 2C depicts the proximal end of an aortic aneurysm in which a sub-neck is present between the aneurysm and a branch vessel.
Figure 2B:
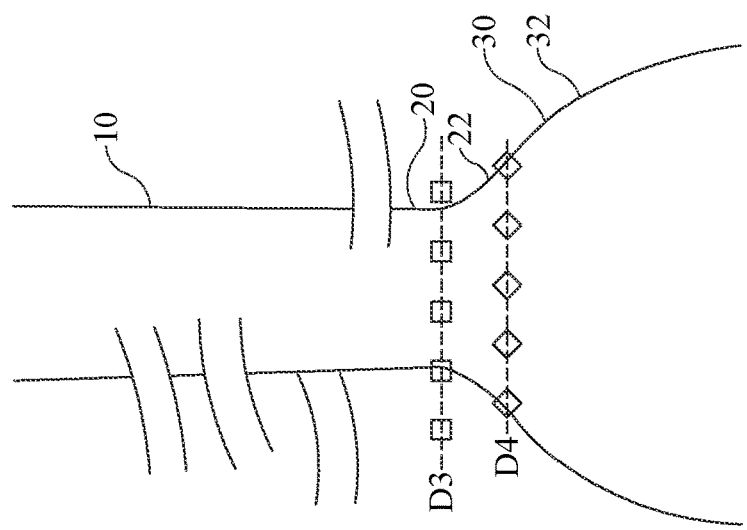
FIG. 2B depicts the proximal end of an aortic aneurysm in which a neck and a sub-neck are present between the aneurysm and a branch vessel.
Figure 2A:
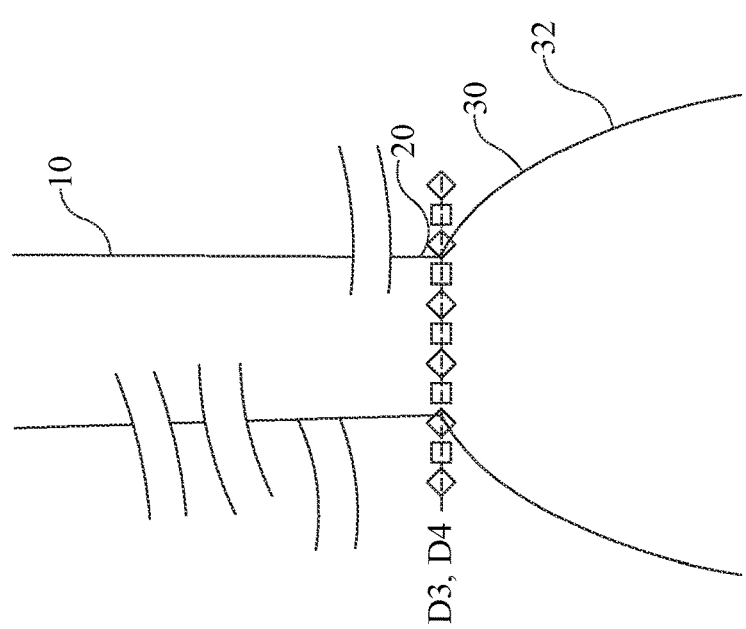
FIG. 2A depicts the proximal end of an aortic aneurysm in which a neck is present between the aneurysm and a branch vessel.

Referring now to FIGS. 2A-2C, the term "Sub-Neck" is analogous to Standard Sub-Seal and denotes the infra-renal portion of the potential Sub-Seal segment and corresponds to the lesser value of (L4-L3) versus L4. Finally, the segment of aneurysm 30 that is not amenable for Sub-Seal (ie, diameter greater than 32 mm or that of the actual device used) is referred to as the Sac 32. For example, as shown in FIG. 2A, where the Point of Divergence (D3) is at the same location as the End of Apposition (D4), the aorta 10 can be said to have only a Neck 20 and a Sac 32. By comparison, as shown in FIGS. 2B and 2C, where there is space between the Point of Divergence (D3) and the End of Apposition (D4), a Sub-Neck 22 is also defined in the location between the Point of Divergence (D3) and the End of Apposition (D4).

Figure 3:
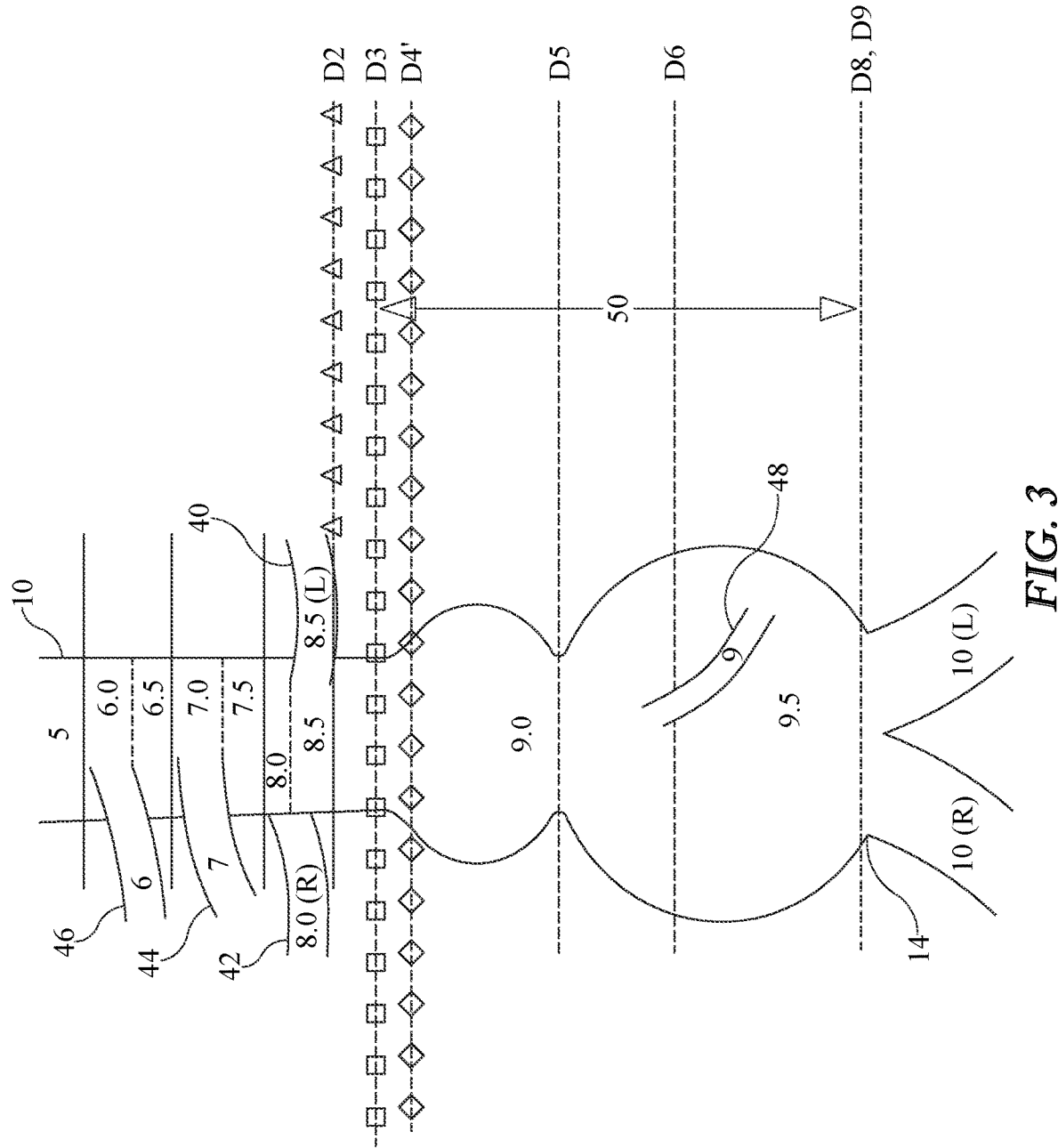
FIG. 3 depicts an aortic aneurysm having a double-bubble or snowman shape illustrating a numbered zone system of the present invention.

For completeness, the terminus 14 of the aorta 10 is considered D9. The distal extent of the aortic aneurysm 30 is defined as the point where the aorta 10 resumes its normal cylindrical or slightly convergent shape and is denoted the Point of Convergence (D8). If the aorta 10 does not resume a normal contour distally then D8=D9, as shown in FIG. 3. Although not expressly shown, in some embodiments of the present invention, an origin of the blood vessel is also identified.

Referring now to FIG. 3, in some cases, an aneurysm 50 takes the shape of a double-bubble or snowman. That is, the contour of the aorta 10 converges or narrows for a short segment, then diverges a second time prior to converging again. If present, that intervening point of narrowing is referred to as a Point of Restriction (D5.) A segment of potential apposition involving the Point of Restriction (D5), can be considered a Zone of Restriction.

The maximum diameter of the aneurysm 50 is referred to as D6 and the flow lumen at that point referred to as D7. The corresponding lengths of any of these points of reference are similarly determined in relation to D2 by convention. It should be noted that the nomenclature is arbitrary and can include additional points of reference such as those of other vessel segments in either an integrated or independent system. Additional characteristics such as the amount of calcification, atheroma, thrombus, dissection, outflow vessels, angulation, etc. can also serve as data points and any combination of data points can be used formulaically to derive additional data points.

Although the terms "zone" and "segment" are often used interchangeably, the term "zone" also implies a specific connotation in terms of anatomic location within the aorta. That is, the Society of Thoracic Surgery has endorsed a numbered zone system that expands on the scheme for the aortic arch originally proposed by Iwinaka to include the remainder of the aorta and into the iliac arteries. The boundaries of the zones are based primarily on the location of the orifice of the important branch vessels of the aorta. Referring still to FIG. 3, for the abdominal aorta 10, Zone 5 refers to the aortic segment proximal to the celiac artery 46. Zone 6 refers to the aortic segment spanning from the proximal edge of the celiac artery 46 to the proximal edge of superior mesenteric artery 44. Zone 7 refers to the aortic segment spanning from the proximal edge of the superior mesenteric artery 44 to the proximal edge of the most proximal renal artery 42. Zone 8 refers to the aortic segment spanning from the proximal edge of the most proximal renal artery 42 to the distal edge of the of the most distal renal artery 40. Zone 9 refers to the aortic segment spanning from the distal edge of the most distal renal artery 40 to the aortic terminus 14.

In accordance with the present invention, and referring now to FIGS. 3, 4A-4C, 5A-5B, and 6A-6B, the numbered zones are further subdivided by decimal places to denote an even more specific location in the aortic tree using a single numerical value. For the abdominal aorta 10, the numeric midpoint of Zones 6, 7, and 9 are the most distal edge of the celiac 46, superior mesenteric 44, and inferior mesenteric arteries 48 respectively. The numerical midpoint of Zone 8 is the most proximal edge of the most distal renal artery 40. For data management, the vessels themselves can also be numbered in correspondence to the Zone that they define.

The practical application of using Sub-Zones is that it is possible to infer the clinical relevance of the location of a Point of Reference. For example, defining the location of the Start of Devices (D1) at Sub-Zone 7.3 infers that the devices not only cover both renal arteries 40, 42 (being proximal to Zone 8), but more precisely that it encroaches on the lumen of the Superior Mesenteric Artery 44 by approximately 40%. Such precise clinically important information cannot be inferred with the current zone system nor by simply knowing the length of L1. Likewise, sub-zones allows inference to the length of the sealing segment, specifically in regards to the location of the Point of Divergence (D3) and the End of Apposition (D4,D4'). For example, a Point of Divergence (D3) location of Sub-Zone 9.0 signifies it is flush to the distal edge of the lowest renal artery 40 (L3=0). Sub-zone 9.1 refers to the segment from 1-5 mm distal to lowest renal artery 40. Sub-zone 9.2 refers to the segment from 6-10 mm distal to lowest renal artery 40. Sub-zone 9.3 refers to the segment from 11-15 mm distal to lowest renal artery 40. Sub-zone 9.4 refers to segment from 16 mm distal to lowest renal artery 40 to the inferior mesenteric artery 48. While in this instance more precise information is available from the L3 and L4 measurements, the practical application of this Sub-zone division is that it allows for grouping of similar anatomic morphologies for comparative purposes using more objective criteria than is currently available. In this system, it is proposed that a Point of Divergence (D3) location of Sub-zone 9.0 infers "Juxtarenal" morphology, Sub-zone 9.1 infers an "Ultra-short" neck, Sub-zone 9.2 infers a "Short" neck, Sub-zone 9.3 infers and "Moderate" neck, and Sub-zone 9.4 infers a "Long" neck. Of course, such definitions can be modified, for example depending on the results of outcomes research, without departing from the spirit and scope of the present invention.

Referring now specifically to FIGS. 4A-4C, it is recognized that aberrant branch vessel anatomy poses significant challenges to any Aortic Zone nomenclature. The most common variants involve the renal arteries, but any branch vessel can exhibit aberrancy. Any contingency for aberrancy should preferably be consistent with the principals of the original zone system. For the common scenario of accessory renal arteries within the vicinity of a normal zone 8, in accordance with the present invention, a second decimal point is added to clarify both the location and total number of renal arteries.

For example, as shown in FIG. 4A, the most proximal renal artery 42 is identified by the nomenclature 8.00 (L) and the most distal renal artery 40 is identified by the nomenclature 8.5 (R). Similarly, as shown in FIG. 4B, in which there is one accessory renal artery, the most proximal renal artery 42 is identified by the nomenclature 8.00 (R), the intermediate renal artery 41 is identified by the nomenclature 8.33 (L), and the most distal renal artery 40 is identified by the nomenclature 8.67 (R). Similarly, as shown in FIG. 4C, in which there are two accessory renal arteries, the most proximal renal artery 42 is identified by the nomenclature 8.00 (R), the proximal intermediate renal artery 43 is identified by the nomenclature 8.25 (L), the distal intermediate renal artery 41 is identified by the nomenclature 8.50 (R), and the most distal renal artery 40 identified by the nomenclature 8.75 (L). As shown in FIGS. 4A-4C as compared to FIG. 3, no changes are made to the nomenclature relating to the superior mesenteric artery 44 or the celiac artery 46 or the corresponding zones.

Figure 5B:
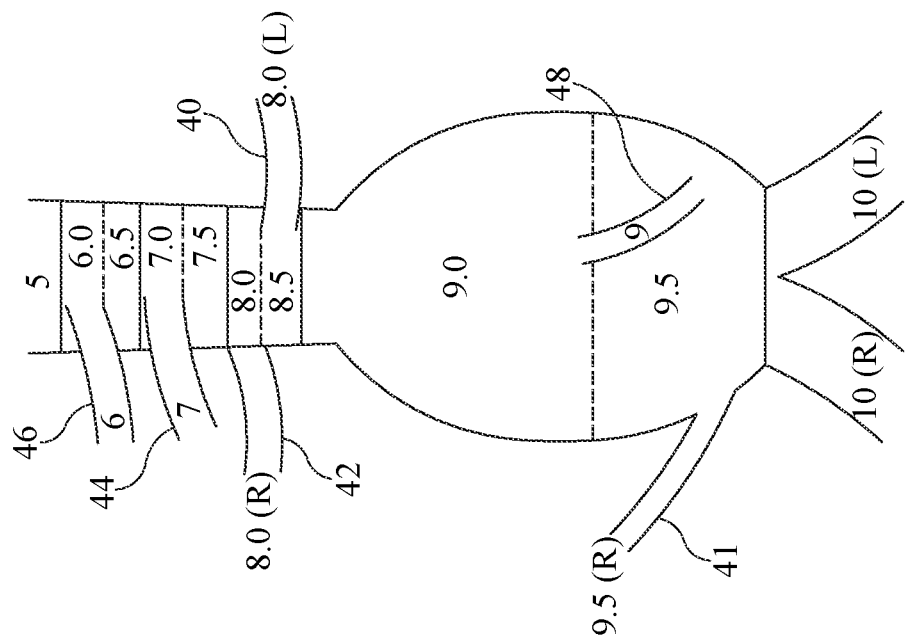
FIG. 5B depicts the proximal end of another aortic aneurysm in which an accessory renal artery is distal to the inferior mesenteric artery illustrating the numbered zone system of the present invention.
Figure 5A:
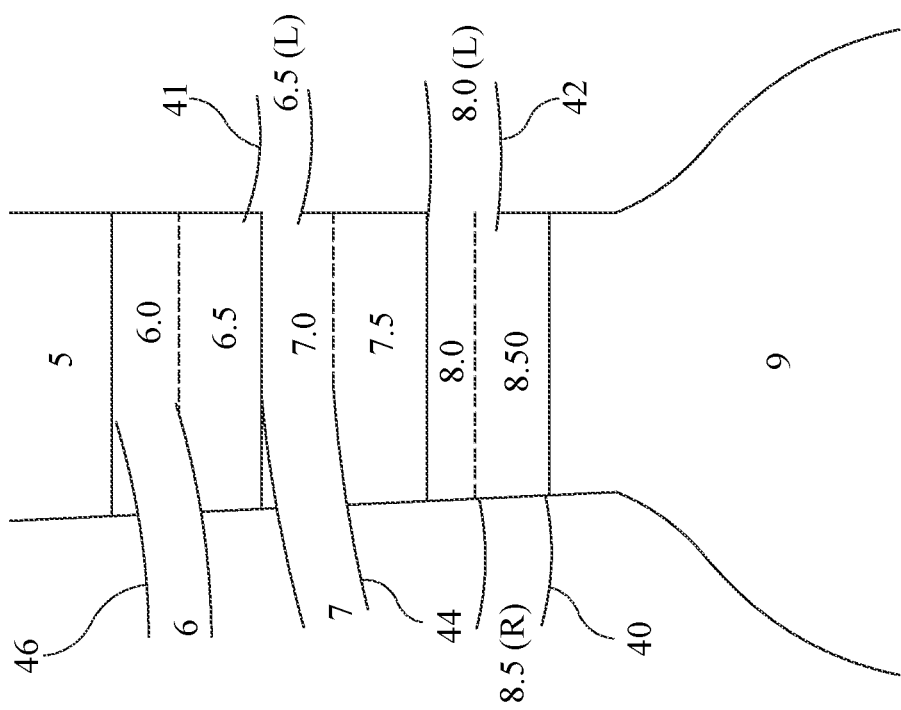
FIG. 5A depicts the proximal end of another aortic aneurysm in which an accessory renal artery arises proximal to the superior mesenteric artery illustrating the numbered zone system of the present invention.

Referring now specifically to FIGS. 5A and 5B, if an accessory renal artery 41 arises proximal to the superior mesenteric artery 44, distal to the inferior mesenteric artery 48, or clearly within an infra-renal aneurysm sac, then the location of the accessory renal artery 41 is assigned to the corresponding zone if it weren't present. For example, as shown in FIG. 5A, in which the accessory renal arises 41 is proximal to the superior mesenteric artery 44, the accessory renal artery 41 is identified by the nomenclature 6.5 (L). Likewise, as shown in FIG. 5B, in which the accessory renal arises 41 is distal to the inferior mesenteric artery 48, the accessory renal artery 41 is identified by the nomenclature 9.5 (R).

Figure 6B:
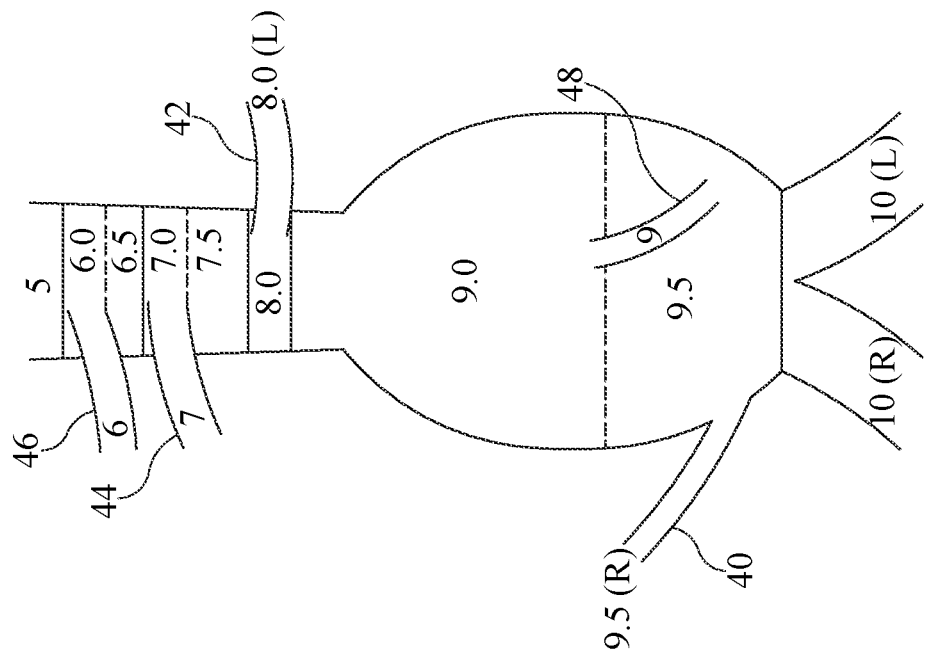
FIG. 6B depicts the proximal end of an aortic aneurysm in which a main renal artery is distal to the inferior mesenteric artery illustrating the numbered zone system of the present invention.
Figure 6A:
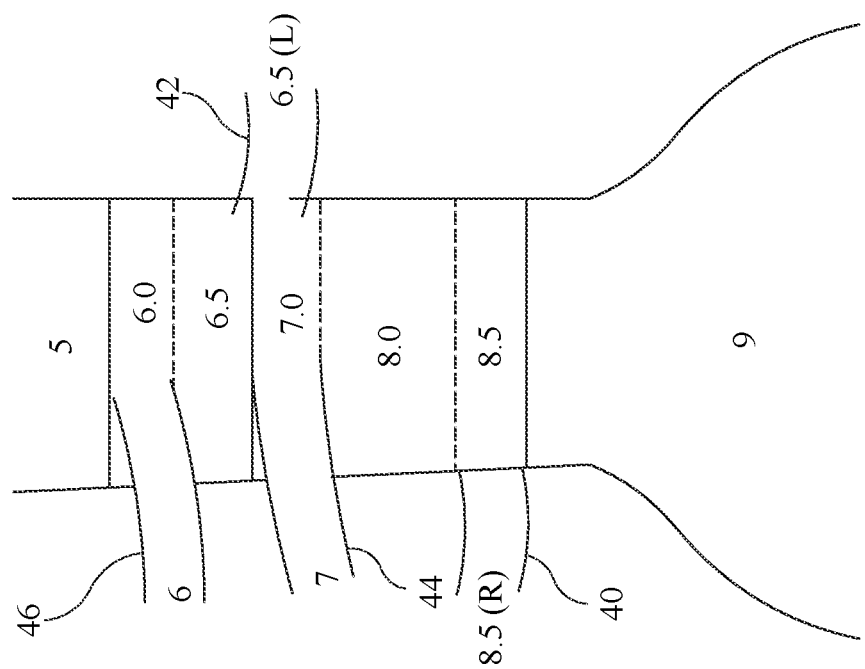
FIG. 6A depicts the proximal end of an aortic aneurysm in which a main renal artery is proximal to the superior mesenteric artery illustrating the numbered zone system of the present invention.

Referring now specifically to FIGS. 6A and 6B, in the absence of accessory renal arteries, the true aberrancy of a main renal artery would warrant a remapping of the Zones. For example, as shown in FIG. 6A, in which the most proximal renal artery 42 is proximal to the superior mesenteric artery 44, the most proximal renal artery 42 is identified by the nomenclature 6.5 (L). Likewise, as shown in FIG. 6B, in which the most distal renal artery 40 is distal to the inferior mesenteric artery 48, the most distal renal artery 40 is identified by the nomenclature 9.5 (R).

Of course, the above examples are non-limiting and a person of ordinary skill would readily understand how to apply the numbered zone system of the present invention to a variety of anatomical situations.

Figure 7:
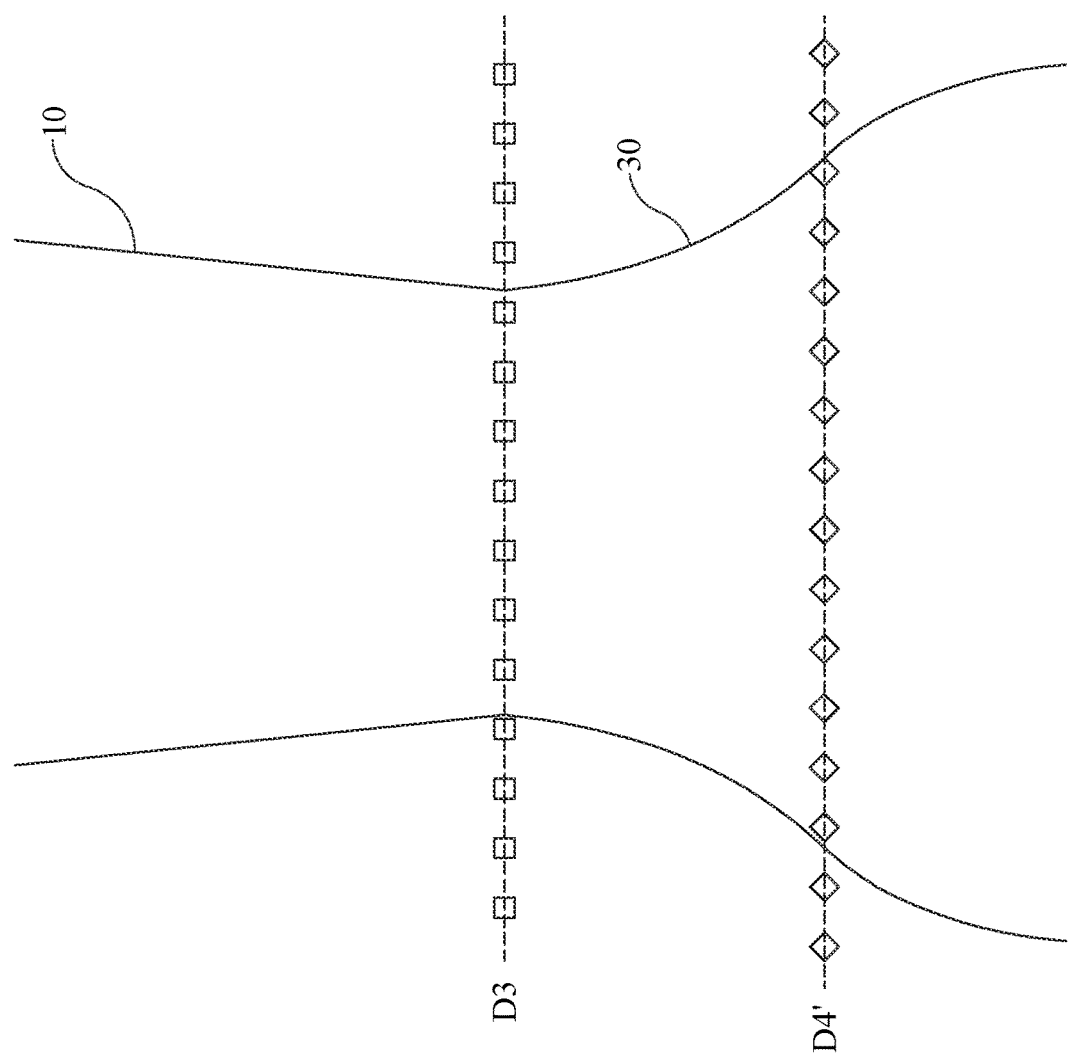
FIG. 7 depicts the proximal end of an aortic aneurysm which demonstrating an End of Apposition that is distal to a Point of Divergence.
Figure 8:
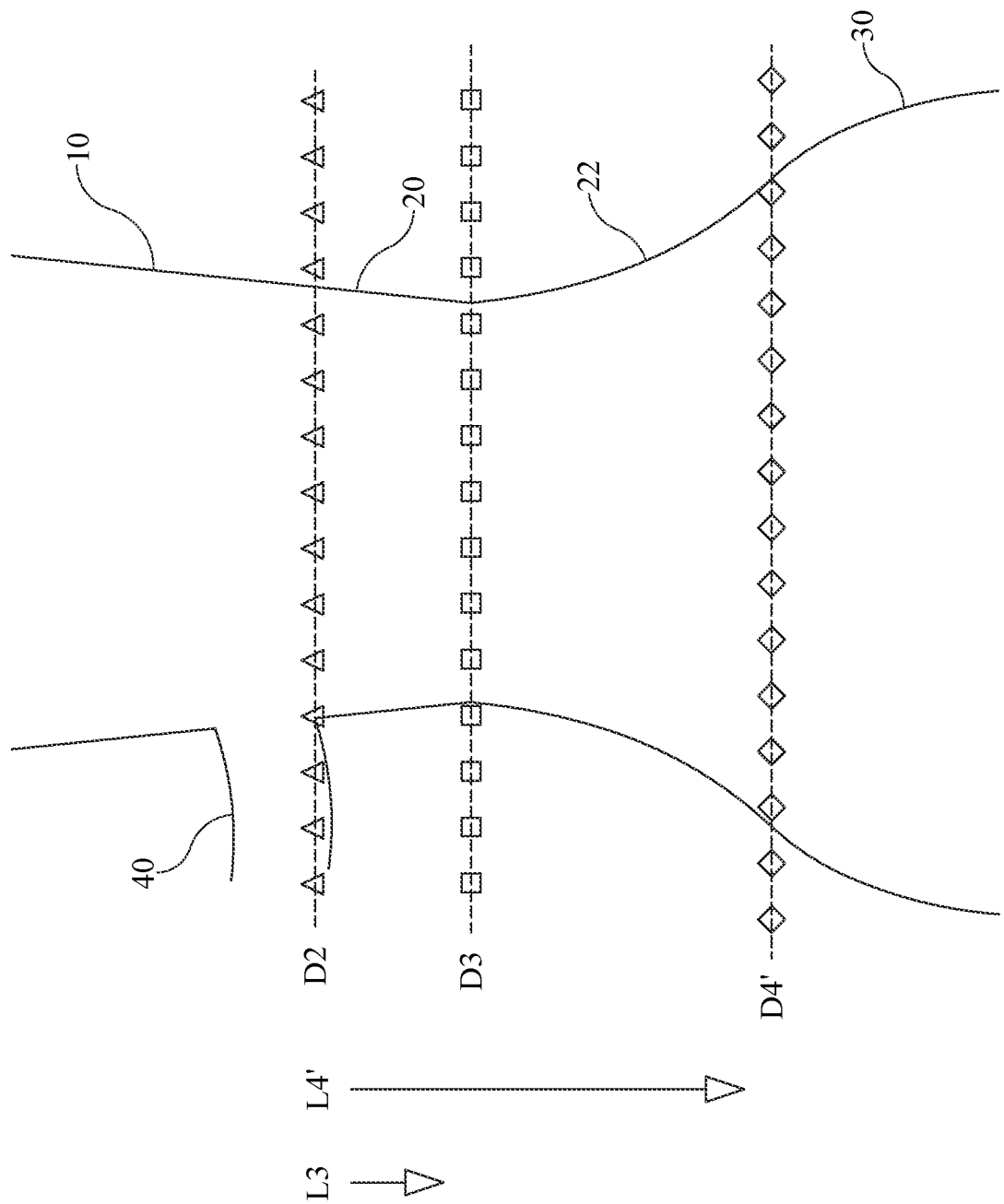
FIG. 8 depicts the proximal end of an aortic aneurysm demonstrating a Phenotype A.

Referring now to FIGS. 7, 8, 9A-9B, and 10A-10B, another advantage of reducing the anatomy to Points of Reference is that specific anatomies can be characterized by the order of such reference points. In this system, each anatomy is grouped into a specific phenotype based on the order of the Points of Reference. The Baseline Phenotypes (prior to repair) are based on the order of the Lowest Preserved Branch Vessel (D2), the Point of Divergence (D3), and the End of Apposition (D4'). In particular, the classification of the aneurysm includes determining which of the seal zone, sub-seal zone, and aneurysm sac contains the Lowest Preserved Branch Vessel. Since baseline sealing characteristics are best defined by the aortic segment immediately distal to the Lowest Preserved Branch Vessel (D2), the classification will default to the inferior phenotype when the location of D2 is the same as D3 or D4'. It is assumed that for an aorta 10 with an aneurysm 30, D4' must be distal to D3, as shown in FIG. 7, Mathematically, there are three sequences that satisfy this assumption. The Baseline Phenotypes are based on these three sequences. As shown in FIG. 8, Phenotype A is based on the sequence D2>D3>D4' moving distally along the aorta 10. In other words, the Lowest Preserved Branch Vessel (D2) is proximal to both the Point of Divergence (D3) and the End of Apposition (D4').

Phenotype A is most favorable phenotype. In the typical case where the Lowest Preserved Branch Vessel is the lowest renal artery 40, Phenotype A contains an infrarenal Standard Seal zone (Neck) 20 and its ensuing potential Standard Sub-Seal zone (Sub-Neck) 22. Conceptually, this phenotype is most associated with standard infrarenal endovascular aneurysm repair.

As shown in FIGS. 9A and 9B, Phenotype B is based on the sequence D3>D2>D4' moving distally along the aorta 10. In other words, the Lowest Preserved Branch Vessel (D2) is at to the Point of Divergence (D3) (FIG. 9A) or distal to the Point of Divergence (D3) (FIG. 9B) but proximal to the End of Apposition (D4').

Phenotype B is the second most favorable phenotype. Returning to the typical case where the Lowest Preserved Branch Vessel is the lowest renal artery 40, Phenotype B does not contain an infrarenal Standard Seal zone (Neck), but does contain a potential Standard Sub-Seal zone (Sub-Neck) 22. Conceptually, standard infrarenal endovascular repair may still be appropriate if L4 is long. Otherwise, complex repair is likely required for long-term durability.

Figure 10B:
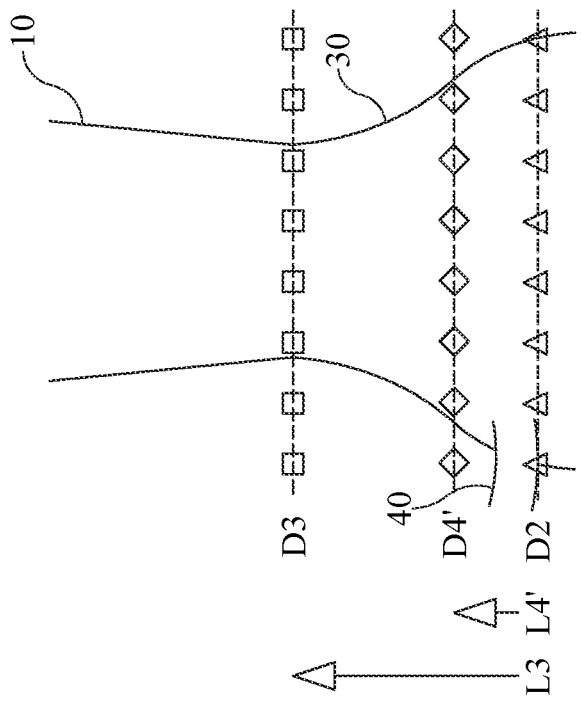
FIG. 10B depicts the proximal end of an aortic aneurysm demonstrating a Phenotype C.
Figure 10A:
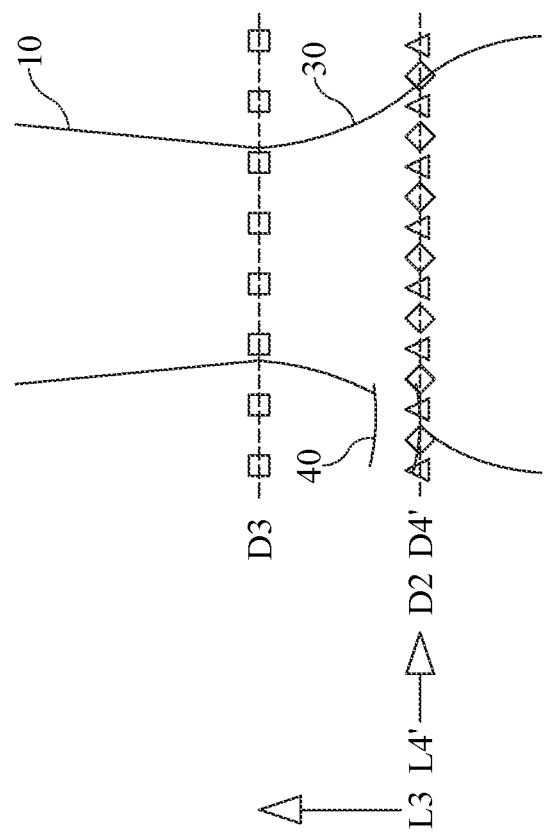
FIG. 10A depicts the proximal end of an aortic aneurysm demonstrating a Phenotype C.

As shown in FIGS. 10A and 10B, Phenotype C is based on the sequence D3>D4'>D2 moving distally along the aorta 10. In other words, the Lowest Preserved Branch Vessel (D2) is at the End of Apposition (D4') (FIG. 10A) or distal to the End of Apposition (D4') (FIG. 10B).

Phenotype C is the least favorable phenotype. There is no potential sealing segment immediately distal to the Lowest Preserved Branch Vessel (e.g, the lowest renal artery 40). Conceptually, complex repair is required for exclusion of the aneurysm in this phenotype.

For convention, the presence of a Point of Restriction (D5) is denoted by adding "Plus" to the phenotype nomenclature to recognize the additional potential apposition zone. For example, a Point of Restriction (D5) in Phenotype B anatomy would be considered Phenotype B Plus (or B+) anatomy.

After repair, each baseline phenotype is subdivided based on the relative location of the Start of Devices (D1). The subdivision represents a crude numeric sealing score, where higher numbers denote the incorporation of more sealing segments and a subdivision of "0" denotes the absence of apposition. It should also be recognized that the location of the potential End of Apposition (D4') used in determining baseline phenotype is based on a theoretical maximum sealing diameter. The actual End of Apposition (D4) achieved with repair can differ significantly from D4' depending on the size and shape of the device used for repair. As such, while the potential End of Apposition (D4') should be distal to the Point of Divergence (D3), the same is not always true for the actual End of Apposition (D4). In many cases, the difference in location between D4 and D4' has minimal impact to the overall sealing effectiveness of the configuration as long as End of Apposition (D4) is distal to the Lowest Preserved Branch Vessel (D2); and, therefore, should not warrant a reclassification of the baseline phenotype. This is denoted in mathematic shorthand with a comma. Finally, the classification will default to the inferior subdivision when the location of D1 is the same as D2 or D3.

Figure 11:
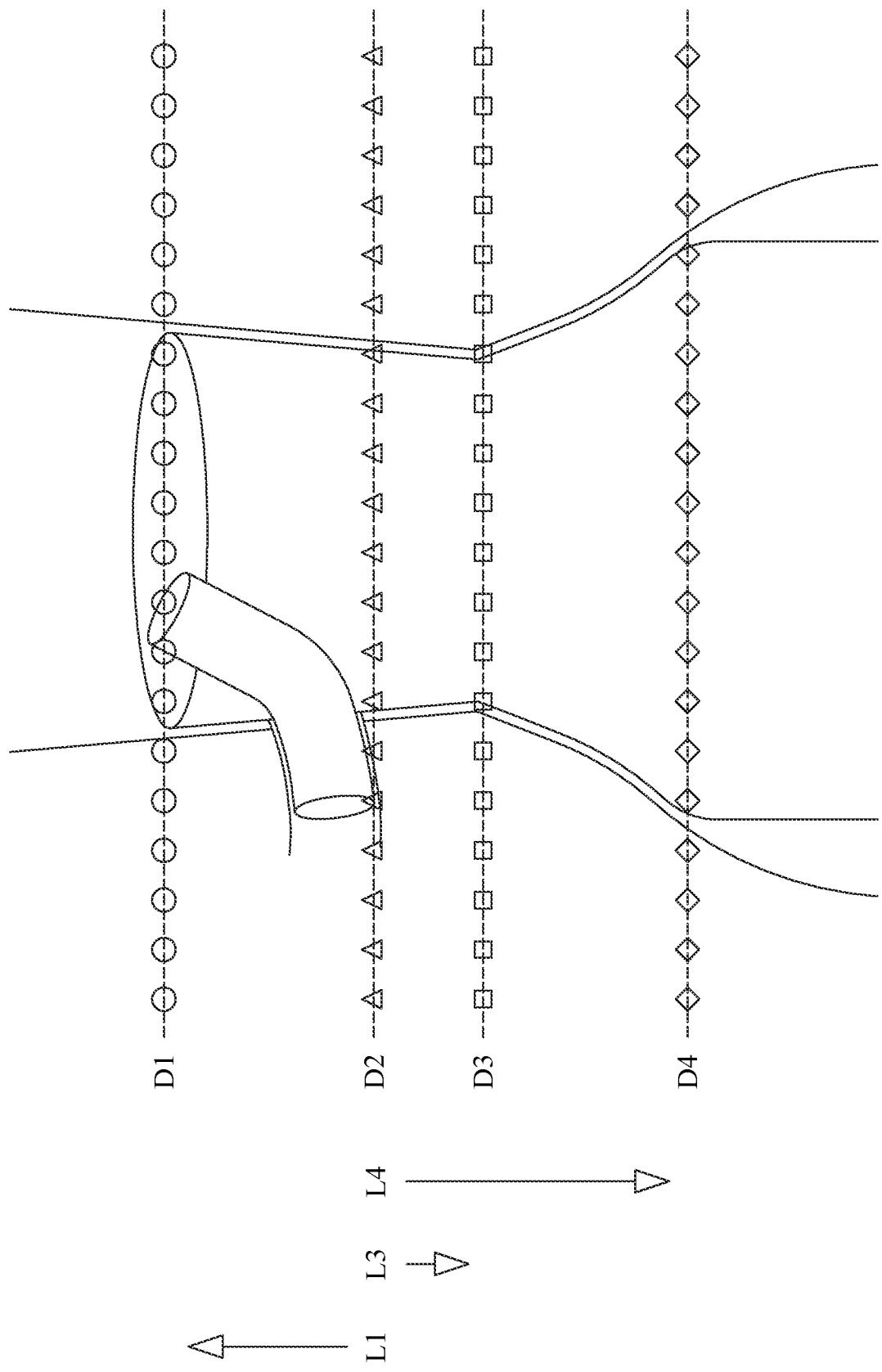
FIG. 11 depicts the proximal end of an aortic aneurysm of a patient's vasculature with a graft deployed within the vasculature demonstrating a Sub-Phenotype A3.

Referring now to FIG. 11, Sub-phenotype A3 is based on the sequence D1>D2>D3, D4. In other words, the Start of Devices (D1) is proximal to the Lowest Preserved Branch Vessel (D2), which in turn is proximal to both the Point of Divergence (D3) and the End of Apposition (D4.) This sub-phenotype is the most secure in terms of sealing effectiveness. It likely involves three sealing segments (or two long ones), including the Complex Seal segment, the Seal segment, and usually the Sub-Seal segment.

Referring now to FIG. 12, Sub-phenotype A2 is based on the sequence D2>D1>D3, D4. In other words, the Start of Devices (D1) is at (FIG. 12A) or distal to (FIG. 12B) the Lowest Preserved Branch Vessel (D2), but is proximal to both the Point of Divergence (D3) and the End of Apposition (D4.) This sub-phenotype likely involves two sealing segments (or one long one), including the Seal segment, and usually the Sub-Seal segment.

Referring now to FIGS. 13A and 13B, Sub-phenotype A1 is based on the sequence D2>D3>D1>D4. In other words, the Start of Devices (D1) is distal to the Lowest Preserved Branch Vessel (D2), at (FIG. 13A) or distal to (FIG. 13B) the Point of Divergence, but is proximal to the End of Apposition (D4.) This sub-phenotype involves only one sealing segment, the Sub-Seal segment.

Referring now to FIG. 14, Sub-phenotype A0 is based on the sequence D2>D3>D4'>D1. In other words, since there is no achieved apposition, the Start of Devices (D1) is distal to the Lowest Preserved Branch Vessel (D2), the Point of Divergence (D3), and the potential End of Apposition (D4'.) This sub-phenotype generally indicates a slipped or undersized endograft.

Figure 15:
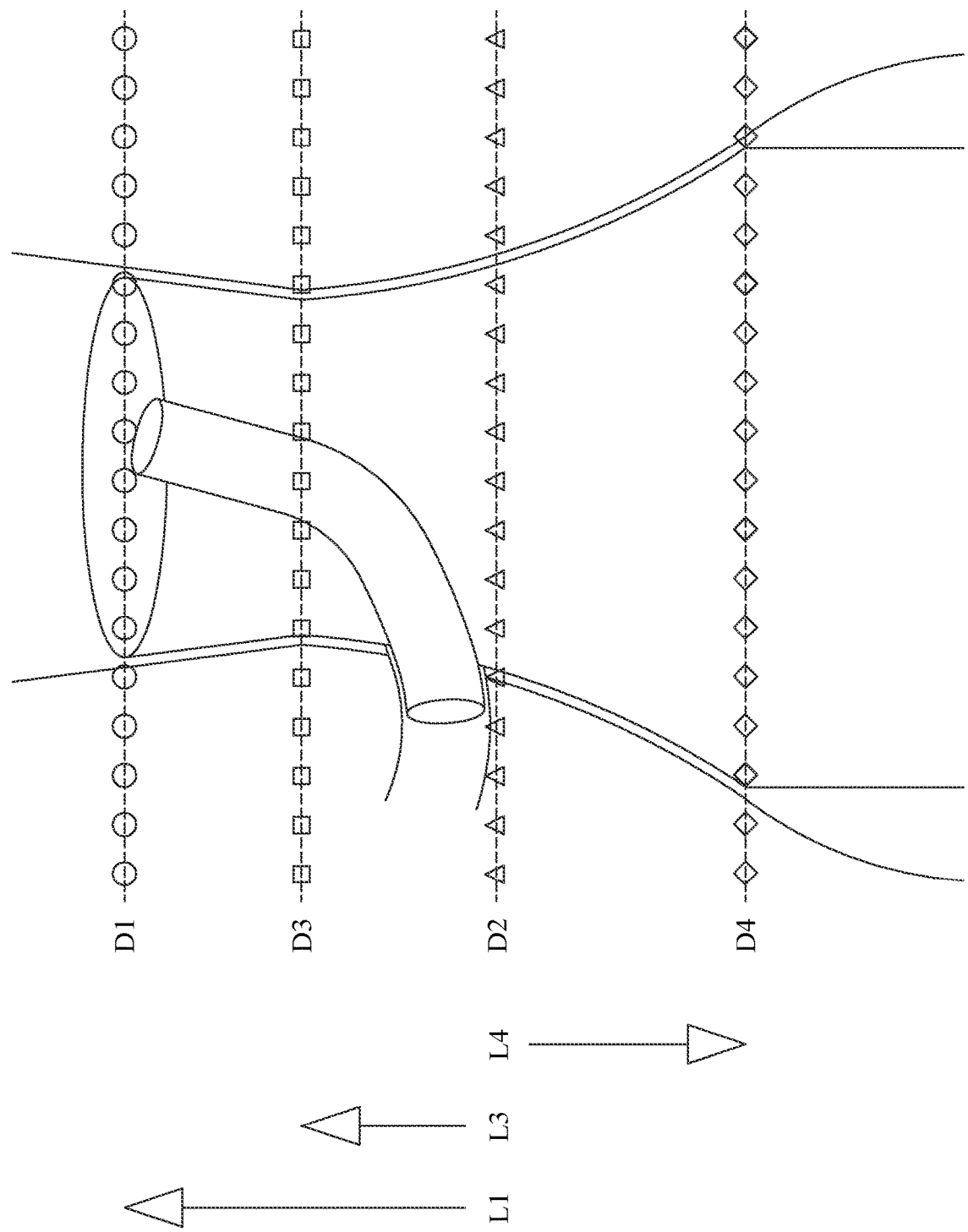
FIG. 15 depicts the proximal end of an aortic aneurysm of a patient's vasculature with a graft deployed within the vasculature demonstrating a Sub-Phenotype B3.

Referring now to FIG. 15, Sub-phenotype B3 is based on the sequence D1>D3>D2>D4. In other words, the Start of Devices (D1) is proximal to the Point of Divergence (D3), the Lowest Preserved Branch Vessel (D2), and the End of Apposition (D4.) This sub-phenotype likely involves three sealing segments, including the Complex Seal segment, the Complex Sub-Seal segment (if one exists), and the Sub-Seal segment.

Referring now to FIGS. 16A and 16B, Sub-phenotype B2 is based on the sequence D3>D1>D2>D4. In other words, the Start of Devices (D1) is at (FIG. 16A) or distal to (FIG. 16B) the Point of Divergence (D3), but proximal to the Lowest Preserved Branch Vessel (D2), and the End of Apposition (D4.) This sub-phenotype involves two sealing segments, including the Complex Sub-Seal segment, and the Sub-Seal segment.

Referring now to FIGS. 17A and 17B, Sub-phenotype B1 is based on the sequence D3>D2>D1>D4. In other words, the Start of Devices (D1) is at (FIG. 17A) or distal to (FIG. 17B) both the Point of Divergence (D3) and the Lowest Preserved Branch Vessel (D2), but proximal to the End of Apposition (D4.) Similar to A1, this sub-phenotype involves only one sealing segment, the Sub-Seal segment.

Figure 18:
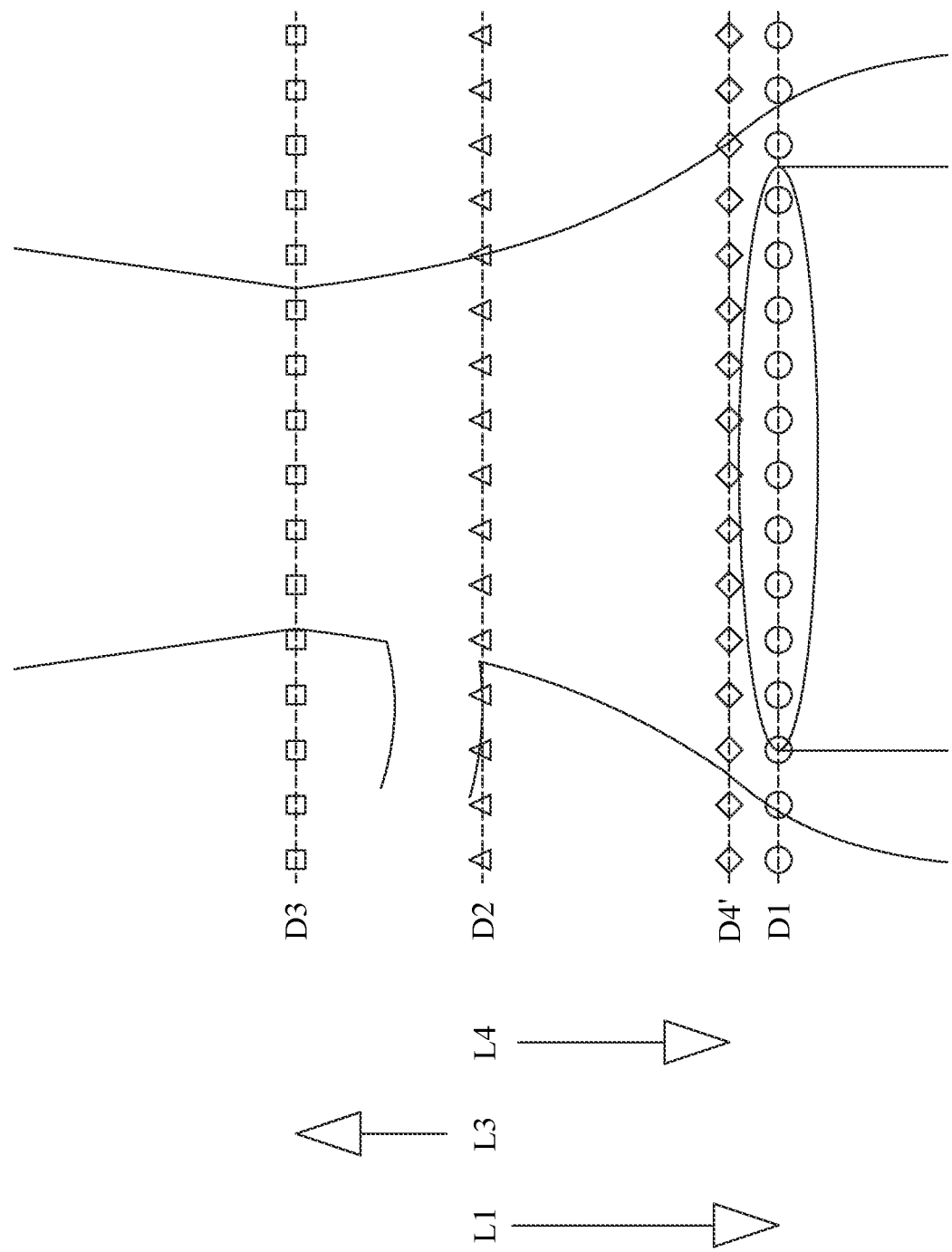
FIG. 18 depicts the proximal end of an aortic aneurysm of a patient's vasculature with a graft deployed within the vasculature demonstrating a Sub-Phenotype B0.

Referring now to FIG. 18, Sub-phenotype B0 is based on the sequence D3>D2>D4'>D1. In other words, since there is no achieved apposition, the Start of Devices (D1) is distal to the Point of Divergence (D3), the Lowest Preserved Branch Vessel (D2), and the potential End of Apposition (D4'.) Similar to A0, this sub-phenotype generally indicates a slipped or undersized endograft.

Figure 19:
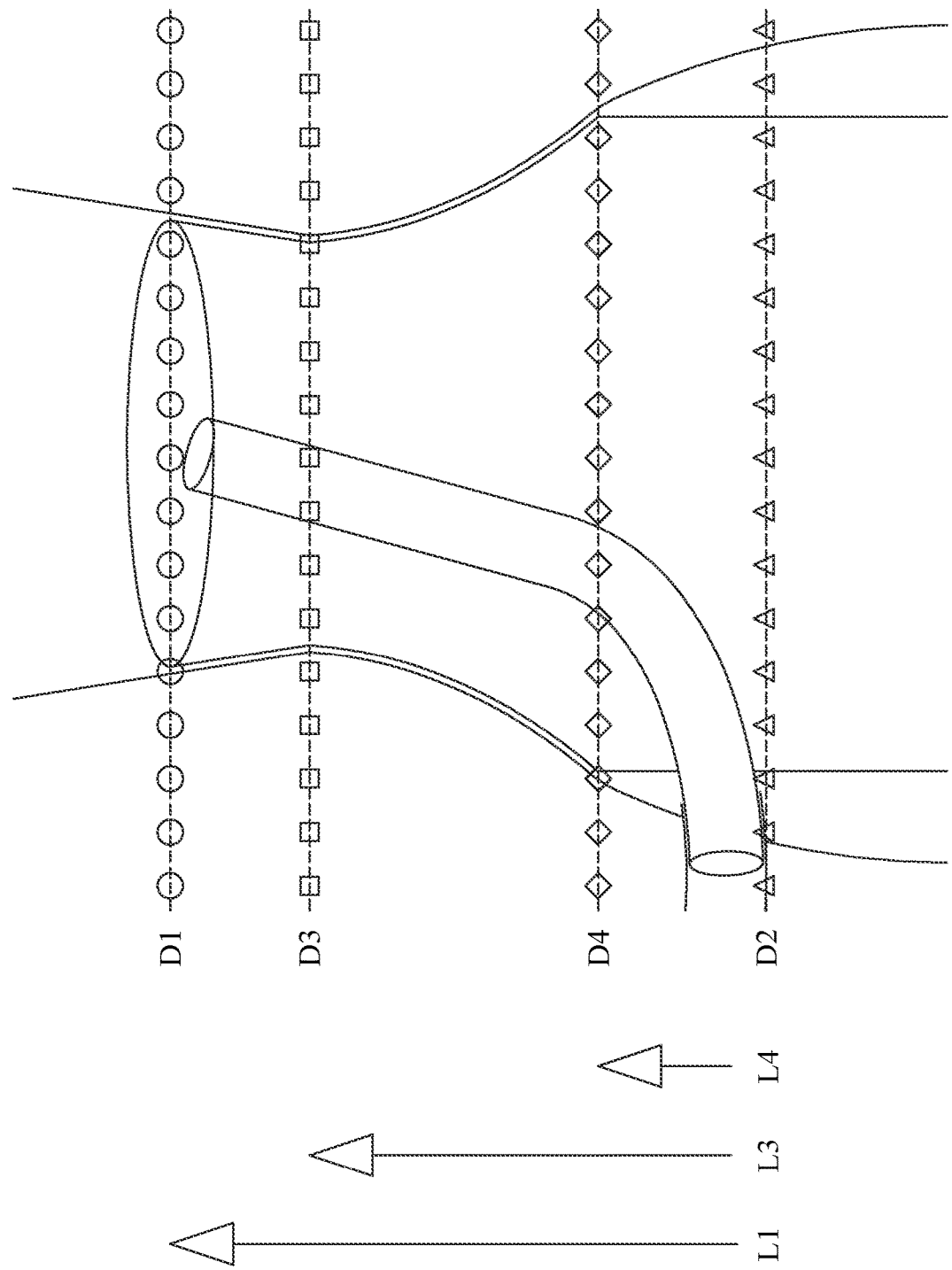
FIG. 19 depicts the proximal end of an aortic aneurysm of a patient's vasculature with a graft deployed within the vasculature demonstrating a Sub-Phenotype C2.

Since baseline Phenotype C entails only two potential sealing segments, there is no Sub-phenotype C3. Referring now to FIG. 19, Sub-phenotype C2 is based on the sequence D1>D3, D4>D2. In other words, the Start of Devices (D1) is proximal to both the Point of Divergence (D3) and the End of Apposition (D4), which in turn are proximal to the Lowest Preserved Branch Vessel (D2), This sub-phenotype likely involves two sealing segments, including the Complex Seal segment, and usually the Complex Sub-Seal segment.

Referring now to FIGS. 20A and 20B, Sub-phenotype C1 is based on the sequence D3>D1>D4>D2. In other words, the Start of Devices (D1) is at (FIG. 20A) or distal to (FIG. 20B) the Point of Divergence (D3), but proximal to the the End of Apposition (D4), which in turn is at or proximal to the Lowest Preserved Branch Vessel (D2). This sub-phenotype involves only one sealing segment, the Complex Sub-Seal segment.

Figure 21:
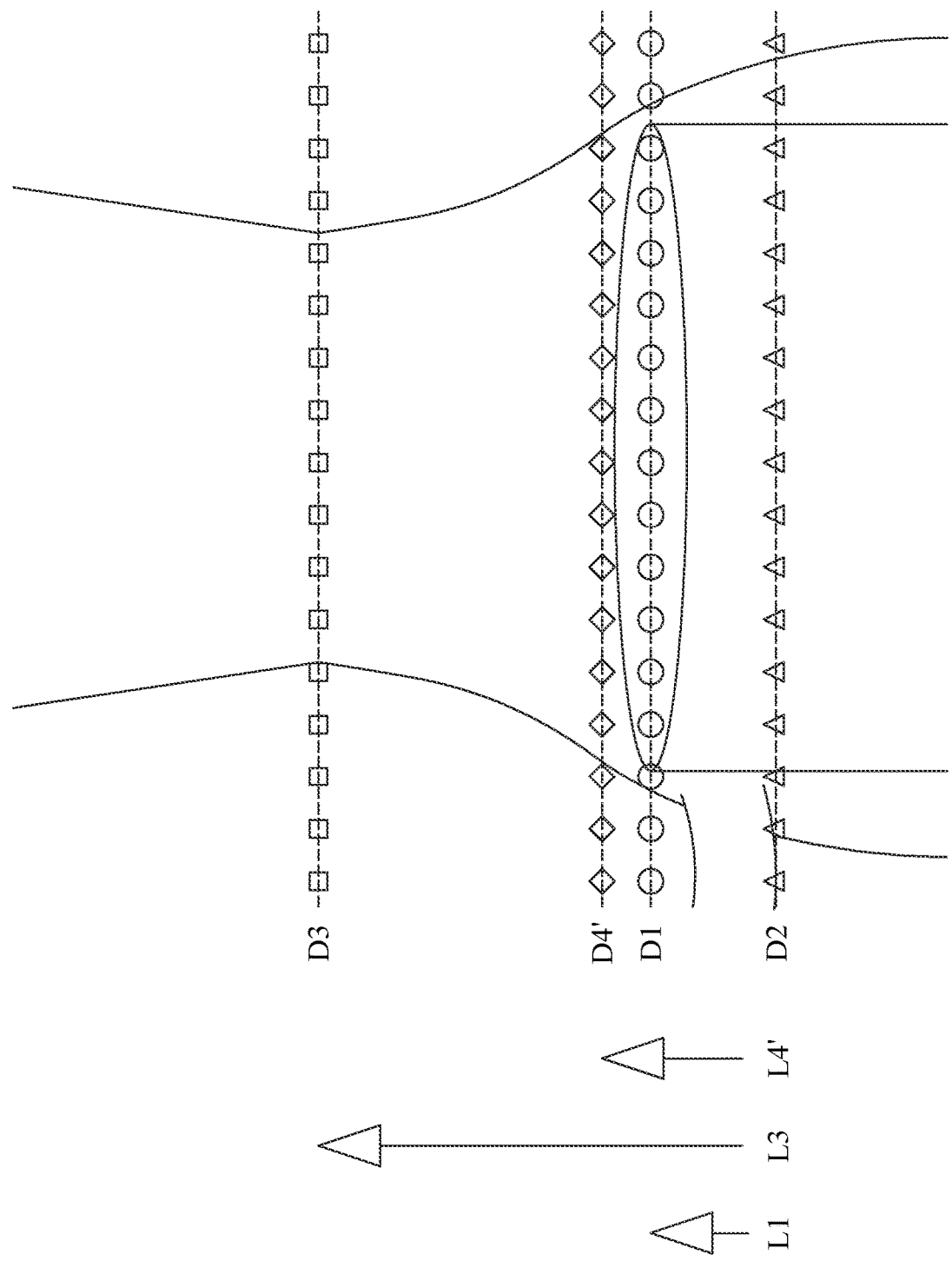
FIG. 21 depicts the proximal end of an aortic aneurysm of a patient's vasculature with a graft deployed within the vasculature demonstrating a Sub-Phenotype C0.

Referring now to FIG. 21, Sub-phenotype C0 is based on the sequence D3>D1<D4'>D2. In other words, since there is no achieved apposition, the Start of Devices (D1) is distal to the Point of Divergence (D3), and the potential End of Apposition (D4'), which in turn is at or proximal to the Lowest Preserved Branch Vessel (D2), Similar to A0 and B0, this sub-phenotype generally indicates a slipped or undersized endograft.

For clarification, since the Start of Devices (D1) is defined as the most proximal end of the fabric covered portion of the main aortic endograft that is at least partially apposed to the wall of the aorta, the D1 of an undersized graft with no apposition to the wall of the aorta is considered distal to the potential End of Apposition (D4') regardless of whether or not the device has physically slipped.

Figure 22A:
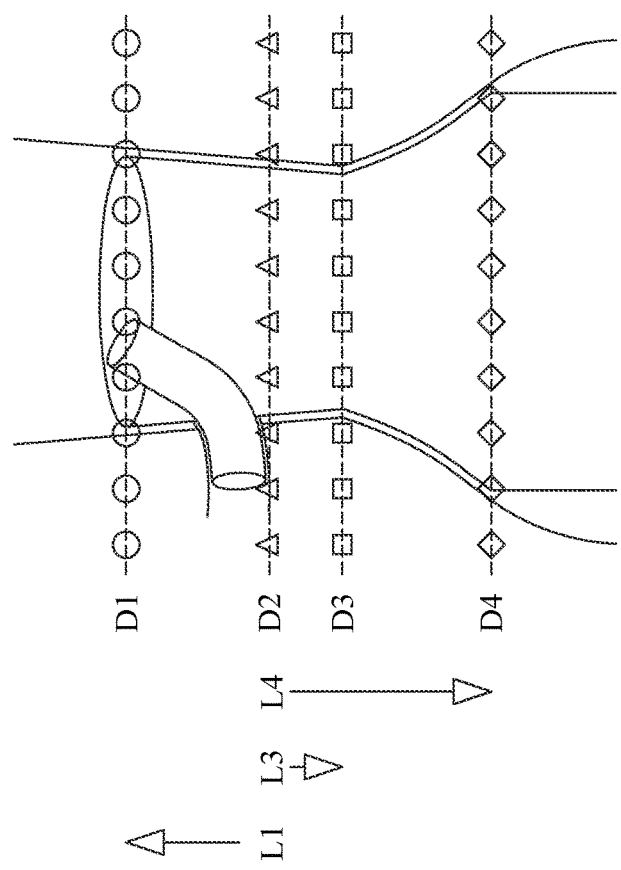
FIG. 22A depicts the proximal end of an aortic aneurysm of a patient's vasculature with a graft deployed within the vasculature demonstrating a Sub-Phenotype A3.
Figure 22B:
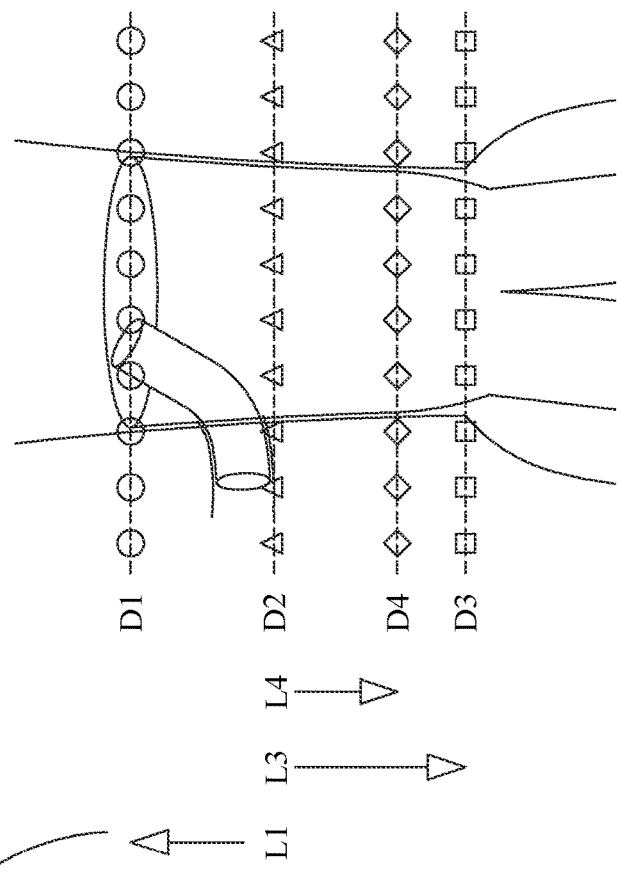
FIG. 22B depicts the proximal end of an aortic aneurysm of a patient's vasculature with a bifurcated graft deployed within the vasculature demonstrating a Sub-Phenotype A3.

Further, as noted previously, the actual End of Apposition (D4) achieved with repair can differ significantly from D4' depending on the size and shape of the device used for repair. In particular, as shown for example in FIG. 22B, bifurcated devices taper as they transition from the cylindrical main body portion to split into two smaller limbs. The length of the cylindrical main body portion proximal to the transition varies from device to device. Even the shortest main body devices are designed to be of sufficient length to achieve adequate apposition to the wall of the aorta in straightforward anatomy. In most cases then, including some complex repairs, any "unrealized" apposition is related to the presence of a relatively long potential seal zone and will not compromise the effectiveness of the device to vessel sealing interaction. Therefore, a reclassification of the sub-phenotype is not indicated and so the repairs shown in FIGS. 22A and 22B are both categorized as Sub-phenotype A3.

However, in other cases, the use of a shorter main body device or a tapered cylindrical device can have a significant deleterious impact on the effectiveness of the device to vessel sealing interaction. Specifically, compromise can occur when the use and positioning of such devices unnecessarily places the End of Apposition (D4) proximal to the Lowest Preserved Branch Vessel (D2).

Perhaps this scenario is best illustrated in complex repairs utilizing parallel endografts with reference now to FIGS.

Figure 23A:
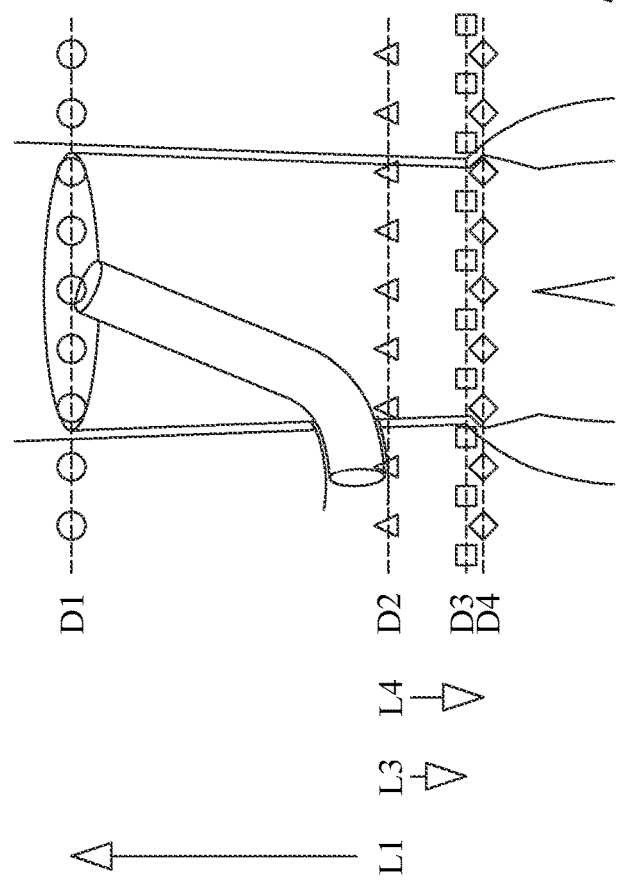
FIG. 23A depicts the proximal end of an aortic aneurysm of a patient's vasculature with a parallel graft deployed within the vasculature demonstrating a Sub-Phenotype A3.
Figure 23B:
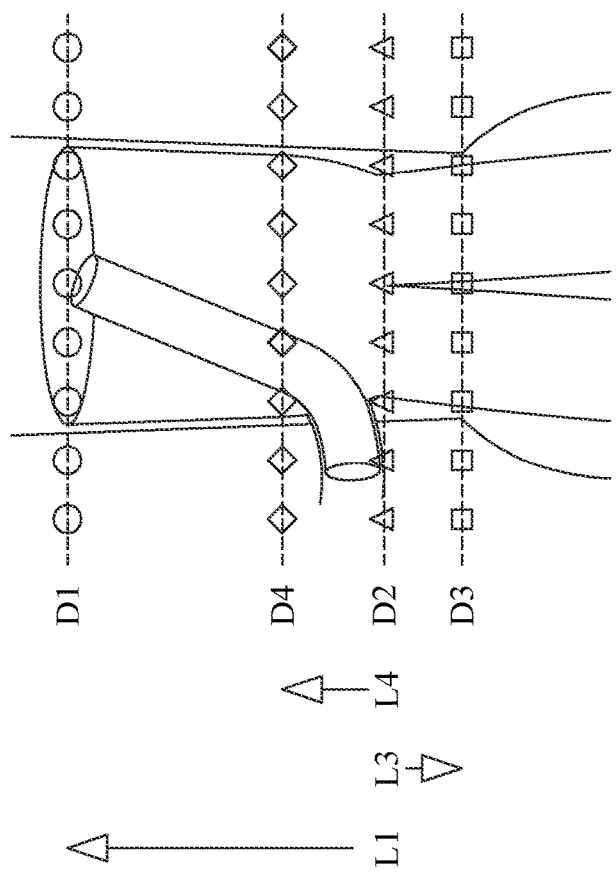
FIG. 23B depicts the proximal end of an aortic aneurysm of a patient's vasculature with a parallel graft deployed within the vasculature demonstrating a Sub-Phenotype C'2.

23A and 23B. Since standard parallel endograft configurations entail a sealing segment with at least two essentially cylindrical devices alongside each other, there is an inherent mismatch between the overall shape of the aggregate device configuration and the shape of the aorta in these segments. This mismatch often results in gaps in apposition between the combined devices and the wall of the aorta known as gutters, leaving the potential for an endoleak and continued pressurization of the aneurysmal sac. However, the recruitment of an additional sealing segment distal to the Lowest Preserved Branch Vessel (D2) with circumferential apposition provides a barrier against the transmission of any endoleak from the more proximal complex sealing segments to the aneurysm sac. Therefore, it is important in the sub-phenotypes A3, B3, and B2 that the apposition of the device extends distal to the Lowest Preserved Branch Vessel (D2) to include that additional barrier of circumferential apposition, as shown in FIG. 23A. If the apposition does not extend distal enough to include the potential sealing segments distal to the Lowest Preserved Branch Vessel (D2), then the apposition pattern is functionally similar to that of the C phenotype and the repair should be re-classified as the C' phenotype to reflect that, as illustrated in FIG. 23B. Sub-phenotypes A3 and B3 should be reclassified to the C'2 sub-phenotype. Sub-phenotype B2 should be reclassified to the C'1 sub-phenotype.

Unfortunately, although the utility of parallel endografting techniques for challenging anatomy in high risk patients has been established in the scientific literature, there are no currently available FDA approved devices designed specifically for parallel endografts and very little consensus as to protocols for their use. While it is intuitive that more overlap in the complex sealing segments can reduce the chance for gutter leaks, aggressive positioning of a shorter main body device designed for infrarenal anatomy may inadvertently lead to placement of the End of Apposition proximal to the Lowest Preserved Branch Vessel as described above.

In this sense, the described Points of Reference system cannot only provide a classification for outcomes research, it can also provide a framework for planning and determining indications for repair when considering the various options available. In particular, the classification of the of the aneurysm as described above can be used to determine which device, or devices, should be implanted within the blood vessel for treatment of the aneurysm. To avoid the issue of reclassification to the much less robust C' phenotype, one must first recognize the presence and importance of non-traditional sealing segments such as the Sub-Neck. Shorter main body endografts can still be used in a manner to include these segments by deploying the device low enough to recruit these segments, then extending their cylindrical portion proximally with an aortic extension cuff to provide adequate overlap in the complex apposition zones. Alternatively, the extension cuff can be deployed first to achieve apposition in the infra-branch segment and then extended proximally with the main body device, known as a Kilt technique. Regardless of the anatomic complexity, the goal of the repair should be to extend proximal to the Point of Divergence (D3) if at all feasible without excessive risk.

A Point of Restriction (D5), if present, likewise represents another key area of potential apposition, especially in Phenotype B+ and C+ anatomy. Similar strategies to incorporate the apposition zone of a Point of Restriction (D5), such as longer main body endografts or the Kilt technique, would be apropos in these instances as well.

Referring now to FIGS. 24A and 24B, another principal based on this system that may help maintain barriers to endoleaks is to minimize the number of parallel grafts that cross the Point of Divergence (D3) and the End of Apposition (D4), as illustrated in FIG. 24A. As noted previously, the circumferential apposition present when these points are distal to a branch vessel preserved with a parallel endograft can prevent the transmission of any gutter leak to the aneurysm sac. Certainly, when the Point of Divergence (D3) is distal (indicating a more secure protective segment of standard seal), the chance of successful exclusion should be high. In phenotype C, there is no apposition distal to the Lowest Preserved Branch Vessel, but there may be potential apposition distal to any other preserved branch vessel. If the Lowest Preserved Branch Vessel is preserved in antegrade fashion, then it will need to cross D3 and D4 and potentially compromise the barriers that are protecting the sac from any gutter leaks related to the more proximal preserved branch vessels. Treatment of any endoleak from this compromise may necessitate proximal extension of the devices into aortic segments with other branch vessels, further adding complexity to case and the risk of complications. If instead, the lowest branch vessel is preserved in retrograde fashion, as shown in FIG. 24B, then an external portion of a parallel branch stent of the parallel endograft will not cross D3 or D4. When considered singularly, the more proximal preserved vessels are now treated with the more secure equivalent of an A3, B3, or B2 sub-phenotype. The Lowest Preserved Branch Vessel still proposes a risk for endoleak, but it can likely be treated more easily by isolating its seal mechanism from other preserved branch vessels. Multiple treatment options can be used, but one that relies on parallel endografts involves a sandwich technique. In this technique, the parallel stents are contained (or sandwiched) within the lumen of another device rather than a vessel such as the aorta. The parent device is deployed first and establishes a prosthetic sealing segment that was not otherwise present in the native anatomy.

Figure 25A:
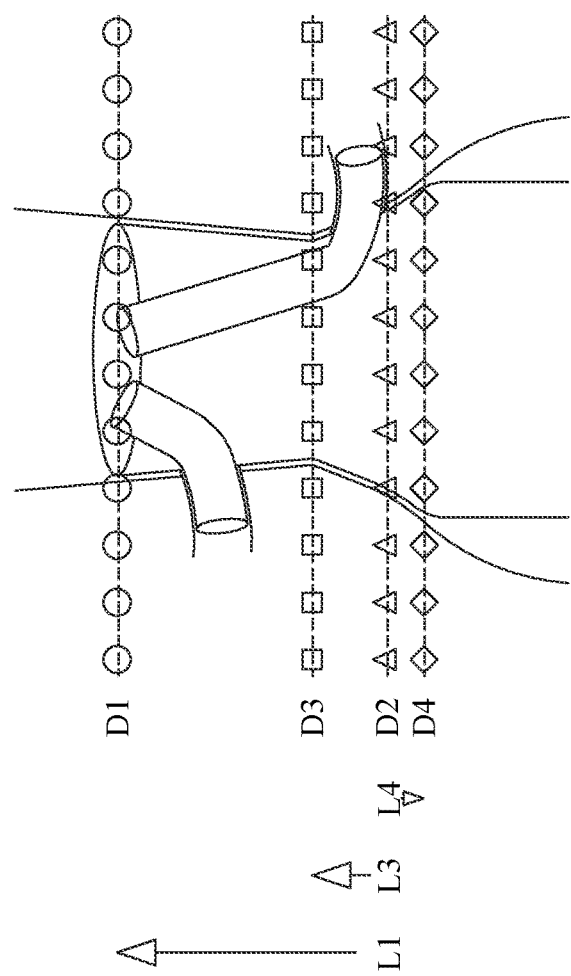
FIG. 25A depicts the proximal end of an aortic aneurysm of a patient's vasculature in which an antegrade parallel graft crosses the Point of Divergence.
Figure 25B:
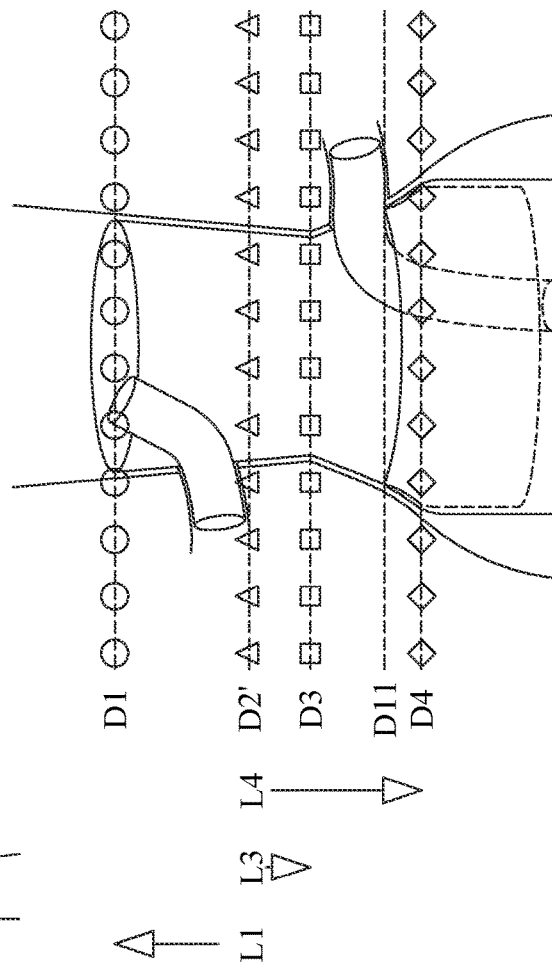
FIG. 25B depicts the proximal end of an aortic aneurysm of a patient's vasculature with a parallel graft deployed within the vasculature using a sandwich technique.

Referring now to FIGS. 25A and 25B, in phenotype B, there is no Seal distal to the Lowest Preserved Branch Vessel, but there is Sub-Seal. If the Lowest Branch Vessel is preserved using an antegrade parallel graft, as shown in FIG. 25A, then an external portion of a parallel branch stent of the parallel endograft will necessitate crossing the Point of Divergence (D3), compromising the seal segment. While it appears that retrograde preservation will similarly necessitate crossing the End of Apposition (D4), any compromise can be avoided using the sandwich technique, as shown in FIG. 25B, by positioning the sealing end of the parent device within the sub-seal segment. Since the parallel grafts are subsequently positioned within the prosthetic sealing segment internal to the parent device, there is no functional crossing of the End of Apposition. The transition point where the parallel grafts are now contained within the parent device will be defined as the Point of Internalization.

Although the above discussion was focused on aneurysms of the aorta, the Points of Reference system can be adapted to any other blood vessel or other segments of the aorta. As an example, for descending thoracic aortic aneurysms, the renovisceral vessels now become relevant to the distal sealing segment of the repair. Point of Divergence is replaced with the Point of Convergence and the sealing complexity is now reversed, increasing as the End of Devices moves distally and the Highest Preserved Branch Vessel becoming the focal point.

In some embodiments of the present invention, the above-described methods for classification are preferably achieved through the use of a digital computer program (i.e., computer-readable instructions executed by a processor of a computer) that includes appropriate modules for executing the requisite instructions (which are stored in a memory component or similar computer-readable medium). Thus, an exemplary system for anatomic classification of blood vessel anatomy in aneurysms in accordance with the present invention may also be characterized as including: (a) a data receiving module for receiving an image of a blood vessel; and (b) an analysis module for (i) analyzing the image to identify a point of divergence of the blood vessel and one or more additional points of reference of the blood vessel, (ii) measuring one or more distances between the point of divergence of the blood vessel and at least one of the one or more additional points of reference, and (iii) classifying the aneurysm based upon the measured distances Preliminary studies utilizing the Point of Reference system for outcomes research has yielded some important early findings. First, it appears that late proximal neck failures occur predominantly when the Start of Devices (D1) is distal to the Point of Divergence (D3). Even cases with seemingly favorable infrarenal anatomy due to the presence of a Point of Restriction (D5) in the subseal zone (i.e., Phenotype B+ or C+ anatomy) are prone to late failure if the Start of Devices (D1) is not extended proximal to the Point of Divergence (D3). Further, the location of the Point of Divergence (D3) in relation to the renal and visceral branch vessels (i.e., specific aortic zone) does not change over time. In other words, the segments of the aorta at high risk for degeneration can be identified very early in the disease process using the Point of Reference system.

These early findings indicate that the Point of Divergence (D3) is an exceptionally important boundary parameter for long term success in endovascular aneurysm repair and that treatment strategies, including the design of devices, should aim to extend the repair proximal to the Point of Divergence. Device specific modifications, such as the addition of branches or fenestrations, are one way to achieve this goal. A modular system, such as one that utilizes parallel endografts, is another potential method.

The other components of the Point of Reference system have relevance to treatment strategies and device designs as well. As alluded to previously, the Point of Reference system can help guide appropriate parallel graft configurations to avoid crossing the Point of Divergence (D3) and/or the End of Apposition (D4) with the externalized portion of the parallel graft. Extending the main body of an aortic graft with strategies such as the Kilt technique can sometimes be important to recruit apposition at the Point of Divergence (D3) or a Point of Restriction (D5) in both device specific and modular designs. These are just some examples of how the Point of Reference system can be used to target therapies.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of anatomic classification of aorta anatomy in aortic aneurysms to determine a number of seal segments between the aorta and an endograft implanted within the aorta, the method comprising:
   accessing an image of an aorta;
   analyzing the image to identify a point of divergence of the aorta and one or more additional points of reference of the aorta, the point of divergence defined as a point along a centerline of the aorta where a contour of the aorta changes from a cylindrical or conical shape to a reverse conical shape, and the one or more additional points of reference including a location of a lowest preserved branch vessel and a location of where a proximal end of an endograft would be upon implantation within the aorta;
   measuring one or more longitudinal distances along the centerline of the aorta between the point of divergence of the aorta and at least one of the one or more additional points of reference; and
   classifying the aneurysm based upon the measured distances to determine a number of seal segments between the aorta and the endograft upon implantation within the aorta;
   wherein, when the location of the proximal end of the endograft is proximal to both the point of divergence and the location of the lowest preserved branch vessel, there are three possible seal segments between the aorta and the endograft upon implantation within the aorta;
   wherein, when the location of the proximal end of the endograft is proximal to only one of the point of divergence and the location of the lowest preserved branch vessel, there are two possible seal segments between the aorta and the endograft upon implantation within the aorta; and
   wherein, when the location of the proximal end of the endograft is distal to both the point of divergence and the location of the lowest preserved branch vessel, there is one possible seal segment between the aorta and the endograft upon implantation within the aorta.

2. The method of claim 1, wherein the one or more additional points of reference includes at least one of: (i) an origin of the aorta, (ii) a terminus of the aorta, (iii) a location of one or more branch vessels, (iv) a point of threshold diameter of the aorta, (v) a point of restriction of the aorta, (vi) a point of maximum diameter of the aorta, and (vii) a point of convergence of the aorta.

3. The method of claim 2, wherein one of the one or more distances measured is a distance between the point of divergence of the aorta and the location of the lowest preserved branch vessel.

4. The method of claim 2, wherein one of the one or more distances measured is a distance between the point of divergence of the aorta and the point of threshold diameter of the aorta.

5. The method of claim 2, wherein the classification of the aneurysm includes identifying the following segments of the aorta:
   a seal zone proximal to the point of divergence;
   a sub-seal zone distal to the point of divergence, but proximal to the point of threshold diameter of the aorta; and
   an aneurysm sac distal to the point of threshold diameter of the aorta.

6. The method of claim 5, wherein the classification of the aneurysm further includes determining which of the segments of the aorta contains the lowest preserved branch vessel.

7. The method of claim 1, wherein the image is further analyzed to identify a location of where an end of apposition of the endograft would be upon implantation within the aorta.

8. The method of claim 7, wherein the threshold diameter of the aorta is a maximum diameter of therapeutic effectiveness of the endograft.

9. The method of claim 7, wherein the threshold diameter of the aorta is a maximum diameter of the endograft.

10. The method of claim 1, wherein one of the one or more distances measured is a distance between the location of the proximal end of the endograft and the location of the lowest preserved branch vessel.

11. The method of claim 1, wherein one of the one or more distances measured is a distance between the point of divergence of the aorta and a point where a diameter of the aorta is a maximum diameter of therapeutic effectiveness of the endograft.

12. A system for anatomic classification of aorta anatomy in aortic aneurysms to determine a number of seal segments between the aorta and an endograft implanted within the aorta, comprising:
   a data receiving module for receiving an image of an aorta; and
   an analysis module for
      i. analyzing the image to identify a point of divergence of the aorta and one or more additional points of reference of the aorta, the point of divergence defined as a point along a centerline of the aorta where a contour of the aorta changes from a cylindrical or conical shape to a reverse conical shape, and the one or more additional points of reference including a location of a lowest preserved branch vessel and a location of where a proximal end of an endograft would be upon implantation within the aorta,
      ii. measuring one or more longitudinal distances along the centerline of the aorta between the point of divergence of the aorta and at least one of the one or more additional points of reference, and
      iii. classifying the aneurysm based upon the measured distances to determine a number of seal segments between the aorta and the endograft upon implantation within the aorta;
   wherein, when the location of the proximal end of the endograft is proximal to both the point of divergence and the location of the lowest preserved branch vessel, there are three possible seal segments between the aorta and the endograft upon implantation within the aorta;
   wherein, when the location of the proximal end of the endograft is proximal to only one of the point of divergence and the location of the lowest preserved branch vessel, there are two possible seal segments between the aorta and the endograft upon implantation within the aorta; and
   wherein, when the location of the proximal end of the endograft is distal to both the point of divergence and the location of the lowest preserved branch vessel, there is one possible seal segment between the aorta and the endograft upon implantation within the aorta.

13. A method of using objective points of reference for the anatomic classification of aortic aneurysms to guide therapy based upon a number of seal segments between the aorta and an endograft implanted within the aorta, the method comprising:

accessing an image of an aorta;

analyzing the image to identify objective points of reference including a point of divergence of the aorta and one or more additional points of reference of the aorta, the point of divergence defined as a point along the centerline of the aorta where a contour of the aorta changes from a cylindrical or conical shape to a reverse conical shape, and the one or more additional points of reference including a location of a lowest preserved branch vessel and a location of where a proximal end of an endograft would be upon implantation within the aorta;

measuring one or more longitudinal distances along the centerline of the aorta between the point of divergence of the aorta and at least one of the one or more additional points of reference;

classifying the aneurysm based upon the measured distances to determine a number of seal segments between the aorta and the endograft upon implantation within the aorta; and developing a treatment strategy based upon the number of seal segments between the aorta and an endograft implanted within the aorta;

wherein, when the location of the proximal end of the endograft is proximal to both the point of divergence and the location of the lowest preserved branch vessel, there are three possible seal segments between the aorta and the endograft upon implantation within the aorta;

wherein, when the location of the proximal end of the endograft is proximal to only one of the point of divergence and the location of the lowest preserved branch vessel, there are two possible seal segments between the aorta and the endograft upon implantation within the aorta; and wherein, when the location of the proximal end of the endograft is distal to both the point of divergence and the location of the lowest preserved branch vessel, there is one possible seal segment between the aorta and the endograft upon implantation within the aorta.

14. The method of claim 13, wherein developing the treatment strategy includes choosing a parallel graft configured for treatment of the aneurysm.

\* \* \* \* \*